United States Patent
Chen et al.

(10) Patent No.: US 12,211,608 B2
(45) Date of Patent: Jan. 28, 2025

(54) SYSTEM AND METHOD FOR NAVIGATING A TOMOSYNTHESIS STACK INCLUDING AUTOMATIC FOCUSING

(71) Applicant: HOLOGIC, INC., Marlborough, MA (US)

(72) Inventors: Jin-Long Chen, Santa Clara, CA (US); Haili Chui, Fremont, CA (US); Kevin Kreeger, Sunnyvale, CA (US); Xiangwei Zhang, Fremont, CA (US)

(73) Assignee: Hologic, Inc., Marlborough, MA (US)

( * ) Notice: Subject to any disclaimer, the term of this patent is extended or adjusted under 35 U.S.C. 154(b) by 297 days.

(21) Appl. No.: 16/853,454

(22) Filed: Apr. 20, 2020

(65) Prior Publication Data
US 2020/0345320 A1    Nov. 5, 2020

Related U.S. Application Data

(63) Continuation of application No. 14/771,696, filed as application No. PCT/US2014/019515 on Feb. 28, 2014, now Pat. No. 10,624,598.
(Continued)

(51) Int. Cl.
*G16H 30/40* (2018.01)
*A61B 6/00* (2024.01)
(Continued)

(52) U.S. Cl.
CPC ............. *G16H 30/40* (2018.01); *A61B 6/025* (2013.01); *A61B 6/463* (2013.01); *A61B 6/469* (2013.01);
(Continued)

(58) Field of Classification Search
CPC ........ G16H 30/20; G16H 30/40; A61B 6/025; A61B 6/463; A61B 6/469; A61B 6/502;
(Continued)

(56) References Cited

U.S. PATENT DOCUMENTS

| | | |
|---|---|---|
| 3,502,878 A | 3/1970 | Stewart |
| 3,863,073 A | 1/1975 | Wagner |

(Continued)

FOREIGN PATENT DOCUMENTS

| | | |
|---|---|---|
| AU | 2014339982 | 4/2015 |
| CN | 1802121 A | 7/2006 |

(Continued)

OTHER PUBLICATIONS

PCT International Search Report for International Patent Appln. No. PCT/US2014/019515, Applicant Hologic, Inc., forms PCT/ISA/210 and 237, mailed Aug. 26, 2014 (10 pages).
(Continued)

*Primary Examiner* — Vincent Rudolph
*Assistant Examiner* — Timothy Choi
(74) *Attorney, Agent, or Firm* — Merchant & Gould P.C.

(57) ABSTRACT

A system and method for reviewing a tomosynthesis image data set comprising volumetric image data of a breast, the method comprising, in one embodiment, causing an image or a series of images from the data set to be displayed on a display monitor and selecting or indicating through a user interface an object or region of interest in a presently displayed image of the data set, thereby causing an image from the data set having a best focus measure of the user selected or indicated object or region of interest to be automatically displayed on the display monitor.

21 Claims, 12 Drawing Sheets

Related U.S. Application Data

(60) Provisional application No. 61/793,437, filed on Mar. 15, 2013.

(51) Int. Cl.

| | | |
|---|---|---|
| *A61B 6/02* | (2006.01) | |
| *A61B 6/46* | (2024.01) | |
| *A61B 6/50* | (2024.01) | |
| *G06F 3/04842* | (2022.01) | |
| *G06F 3/16* | (2006.01) | |
| *G06F 18/22* | (2023.01) | |
| *G06F 18/24* | (2023.01) | |
| *G06T 3/40* | (2024.01) | |
| *G06T 7/00* | (2017.01) | |
| *G06T 11/00* | (2006.01) | |
| *G06T 11/60* | (2006.01) | |
| *G16H 30/20* | (2018.01) | |

(52) U.S. Cl.
CPC ............ *A61B 6/502* (2013.01); *A61B 6/5211* (2013.01); *G06F 3/04842* (2013.01); *G06F 3/167* (2013.01); *G06F 18/22* (2023.01); *G06F 18/24* (2023.01); *G06T 3/40* (2013.01); *G06T 7/0012* (2013.01); *G06T 11/001* (2013.01); *G06T 11/60* (2013.01); *G16H 30/20* (2018.01); *A61B 6/5205* (2013.01); *G06T 2207/10112* (2013.01); *G06T 2207/30068* (2013.01); *G06T 2207/30168* (2013.01)

(58) Field of Classification Search
CPC . A61B 6/5205; A61B 6/5211; G06F 3/04842; G06F 3/167; G06K 9/46; G06K 9/4604; G06K 9/4661; G06K 9/52; G06K 9/6201; G06K 9/6267; G06K 2009/4666; G06T 3/40; G06T 7/0012; G06T 11/001; G06T 11/60; G06T 2207/10112; G06T 2207/30068; G06T 2207/30168
See application file for complete search history.

(56) References Cited

U.S. PATENT DOCUMENTS

| | | |
|---|---|---|
| 3,971,950 A | 7/1976 | Evans et al. |
| 4,160,906 A | 7/1979 | Daniels |
| 4,310,766 A | 1/1982 | Finkenzeller et al. |
| 4,496,557 A | 1/1985 | Malen et al. |
| 4,559,557 A | 12/1985 | Keyes |
| 4,559,641 A | 12/1985 | Caugant et al. |
| 4,706,269 A | 11/1987 | Reina et al. |
| 4,727,565 A | 2/1988 | Ericson |
| 4,744,099 A | 5/1988 | Huettenrauch |
| 4,773,086 A | 9/1988 | Fujita |
| 4,773,087 A | 9/1988 | Plewes |
| 4,819,258 A | 4/1989 | Kleinman et al. |
| 4,821,727 A | 4/1989 | Levene et al. |
| 4,907,156 A | 6/1990 | Doi et al. |
| 4,969,174 A | 11/1990 | Schied |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,099,846 A | 3/1992 | Hardy |
| 5,129,911 A | 7/1992 | Siczek et al. |
| 5,133,020 A | 7/1992 | Giger et al. |
| 5,163,075 A | 11/1992 | Lubinsky |
| 5,164,976 A | 11/1992 | Scheid et al. |
| 5,199,056 A | 3/1993 | Darrah |
| 5,219,351 A | 6/1993 | Teubner |
| 5,240,011 A | 8/1993 | Assa |
| 5,279,309 A | 1/1994 | Taylor et al. |
| 5,280,427 A | 1/1994 | Magnusson |
| 5,289,520 A | 2/1994 | Pellegrino et al. |
| 5,343,390 A | 8/1994 | Doi et al. |
| 5,359,637 A | 10/1994 | Webbe |
| 5,365,562 A | 11/1994 | Toker |
| 5,386,447 A | 1/1995 | Siczek |
| 5,415,169 A | 5/1995 | Siczek et al. |
| 5,426,685 A | 6/1995 | Pellegrino et al. |
| 5,452,367 A | 9/1995 | Bick |
| 5,491,627 A | 2/1996 | Zhang et al. |
| 5,499,097 A | 3/1996 | Ortyn et al. |
| 5,506,877 A | 4/1996 | Niklason et al. |
| 5,526,394 A | 6/1996 | Siczek |
| 5,539,797 A | 7/1996 | Heidsieck et al. |
| 5,553,111 A | 9/1996 | Moore |
| 5,592,562 A | 1/1997 | Rooks |
| 5,594,769 A | 1/1997 | Pellegrino et al. |
| 5,596,200 A | 1/1997 | Sharma |
| 5,598,454 A | 1/1997 | Franetzki |
| 5,609,152 A | 3/1997 | Pellegrino et al. |
| 5,627,869 A | 5/1997 | Andrew et al. |
| 5,642,433 A | 6/1997 | Lee et al. |
| 5,642,441 A | 6/1997 | Riley et al. |
| 5,647,025 A | 7/1997 | Frost et al. |
| 5,657,362 A | 8/1997 | Giger et al. |
| 5,660,185 A | 8/1997 | Shmulewitz et al. |
| 5,668,889 A | 9/1997 | Hara |
| 5,671,288 A | 9/1997 | Wilhelm et al. |
| 5,709,206 A | 1/1998 | Teboul |
| 5,712,890 A | 1/1998 | Spivey |
| 5,719,952 A | 2/1998 | Rooks |
| 5,735,264 A | 4/1998 | Siczek et al. |
| 5,757,880 A | 5/1998 | Colomb |
| 5,763,871 A | 6/1998 | Ortyn et al. |
| 5,769,086 A | 6/1998 | Ritchart et al. |
| 5,773,832 A | 6/1998 | Sayed et al. |
| 5,803,912 A | 9/1998 | Siczek et al. |
| 5,818,898 A | 10/1998 | Tsukamoto et al. |
| 5,828,722 A | 10/1998 | Ploetz |
| 5,835,079 A | 11/1998 | Shieh |
| 5,841,124 A | 11/1998 | Ortyn et al. |
| 5,872,828 A | 2/1999 | Niklason et al. |
| 5,875,258 A | 2/1999 | Ortyn et al. |
| 5,878,104 A | 3/1999 | Ploetz |
| 5,878,746 A | 3/1999 | Lemelson et al. |
| 5,896,437 A | 4/1999 | Ploetz |
| 5,941,832 A | 8/1999 | Tumey |
| 5,954,650 A | 9/1999 | Saito |
| 5,986,662 A | 11/1999 | Argiro |
| 6,005,907 A | 12/1999 | Ploetz |
| 6,022,325 A | 2/2000 | Siczek et al. |
| 6,067,079 A | 5/2000 | Shieh |
| 6,075,879 A | 6/2000 | Roehrig et al. |
| 6,091,841 A | 7/2000 | Rogers |
| 6,091,981 A | 7/2000 | Cundari et al. |
| 6,101,236 A | 8/2000 | Wang et al. |
| 6,102,866 A | 8/2000 | Nields et al. |
| 6,137,527 A | 10/2000 | Abdel-Malek |
| 6,141,398 A | 10/2000 | He |
| 6,149,301 A | 11/2000 | Kautzer et al. |
| 6,175,117 B1 | 1/2001 | Komardin |
| 6,196,715 B1 | 3/2001 | Nambu |
| 6,215,892 B1 | 4/2001 | Douglass et al. |
| 6,216,540 B1 | 4/2001 | Nelson |
| 6,219,059 B1 | 4/2001 | Argiro |
| 6,256,370 B1 | 4/2001 | Yavus |
| 6,233,473 B1 | 5/2001 | Sheperd |
| 6,243,441 B1 | 6/2001 | Zur |
| 6,245,028 B1 | 6/2001 | Furst et al. |
| 6,272,207 B1 | 8/2001 | Tang |
| 6,289,235 B1 | 9/2001 | Webber et al. |
| 6,292,530 B1 | 9/2001 | Yavus |
| 6,293,282 B1 | 9/2001 | Lemelson |
| 6,327,336 B1 | 12/2001 | Gingold et al. |
| 6,327,377 B1 | 12/2001 | Rutenberg et al. |
| 6,341,156 B1 | 1/2002 | Baetz |
| 6,375,352 B1 | 4/2002 | Hewes |

(56) References Cited

U.S. PATENT DOCUMENTS

| | | |
|---|---|---|
| 6,389,104 B1 | 5/2002 | Bani-Hashemi et al. |
| 6,411,836 B1 | 6/2002 | Patel |
| 6,415,015 B2 | 7/2002 | Nicolas |
| 6,424,332 B1 | 7/2002 | Powell |
| 6,442,288 B1 | 8/2002 | Haerer |
| 6,459,925 B1 | 10/2002 | Nields et al. |
| 6,463,181 B2 | 10/2002 | Duarte |
| 6,468,226 B1 | 10/2002 | McIntyre, IV |
| 6,480,565 B1 | 11/2002 | Ning |
| 6,501,819 B2 | 12/2002 | Unger et al. |
| 6,556,655 B1 | 4/2003 | Chichereau |
| 6,574,304 B1 | 6/2003 | Hsieh |
| 6,597,762 B1 | 7/2003 | Ferrant |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes |
| 6,638,235 B2 | 10/2003 | Miller et al. |
| 6,647,092 B2 | 11/2003 | Eberhard |
| 6,650,928 B1 | 11/2003 | Gailly |
| 6,683,934 B1 | 1/2004 | Zhao |
| 6,744,848 B2 | 6/2004 | Stanton |
| 6,748,044 B2 | 6/2004 | Sabol et al. |
| 6,751,285 B2 | 6/2004 | Eberhard |
| 6,758,824 B1 | 7/2004 | Miller et al. |
| 6,813,334 B2 | 11/2004 | Koppe |
| 6,882,700 B2 | 4/2005 | Wang |
| 6,885,724 B2 | 4/2005 | Li |
| 6,901,156 B2 | 5/2005 | Giger et al. |
| 6,912,319 B1 | 5/2005 | Barnes |
| 6,940,943 B2 | 9/2005 | Claus |
| 6,978,040 B2 | 12/2005 | Berestov |
| 6,987,331 B2 | 1/2006 | Koeppe |
| 6,999,553 B2 | 2/2006 | Livingston |
| 6,999,554 B2 | 2/2006 | Mertelmeier |
| 7,022,075 B2 | 4/2006 | Grunwald et al. |
| 7,025,725 B2 | 4/2006 | Dione et al. |
| 7,030,861 B1 | 4/2006 | Westerman |
| 7,110,490 B2 | 9/2006 | Eberhard |
| 7,110,502 B2 | 9/2006 | Tsuji |
| 7,117,098 B1 | 10/2006 | Dunlay et al. |
| 7,123,684 B2 | 10/2006 | Jing et al. |
| 7,127,091 B2 | 10/2006 | OpDeBeek |
| 7,142,633 B2 | 11/2006 | Eberhard |
| 7,218,766 B2 | 5/2007 | Eberhard |
| 7,245,694 B2 | 7/2007 | Jing et al. |
| 7,286,634 B2 | 10/2007 | Sommer, Jr. et al. |
| 7,289,825 B2 | 10/2007 | Fors et al. |
| 7,298,881 B2 | 11/2007 | Giger et al. |
| 7,315,607 B2 | 1/2008 | Ramsauer |
| 7,319,735 B2 | 1/2008 | Defreitas et al. |
| 7,323,692 B2 | 1/2008 | Rowlands |
| 7,346,381 B2 | 3/2008 | Okerlund et al. |
| 7,406,150 B2 | 7/2008 | Minyard et al. |
| 7,430,272 B2 | 9/2008 | Jing et al. |
| 7,443,949 B2 | 10/2008 | Defreitas et al. |
| 7,466,795 B2 | 12/2008 | Eberhard et al. |
| 7,556,602 B2 | 7/2009 | Wang et al. |
| 7,577,282 B2 | 8/2009 | Gkanatsios et al. |
| 7,606,801 B2 | 10/2009 | Faitelson et al. |
| 7,616,801 B2 | 11/2009 | Gkanatsios et al. |
| 7,630,533 B2 * | 12/2009 | Ruth ............... A61B 6/502 |
| | | 382/131 |
| 7,634,050 B2 | 12/2009 | Muller et al. |
| 7,640,051 B2 | 12/2009 | Krishnan |
| 7,697,660 B2 | 4/2010 | Ning |
| 7,702,142 B2 | 4/2010 | Ren et al. |
| 7,705,830 B2 | 4/2010 | Westerman et al. |
| 7,760,924 B2 | 7/2010 | Ruth et al. |
| 7,769,219 B2 | 8/2010 | Zahniser |
| 7,787,936 B2 | 8/2010 | Kressy |
| 7,809,175 B2 | 10/2010 | Roehrig et al. |
| 7,828,733 B2 | 11/2010 | Zhang et al. |
| 7,831,296 B2 | 11/2010 | DeFreitas et al. |
| 7,869,563 B2 | 1/2011 | DeFreitas |
| 7,974,924 B2 | 7/2011 | Holla et al. |
| 7,991,106 B2 | 8/2011 | Ren et al. |
| 8,044,972 B2 | 10/2011 | Hall et al. |
| 8,051,386 B2 * | 11/2011 | Rosander ............... G16H 50/20 |
| | | 715/810 |
| 8,126,226 B2 * | 2/2012 | Bernard ............... G06T 15/20 |
| | | 382/128 |
| 8,155,421 B2 | 4/2012 | Ren et al. |
| 8,165,365 B2 | 4/2012 | Bernard et al. |
| 8,532,745 B2 | 9/2013 | DeFreitas et al. |
| 8,571,289 B2 | 10/2013 | Ruth |
| 8,594,274 B2 | 11/2013 | Hoernig et al. |
| 8,677,282 B2 | 3/2014 | Cragun et al. |
| 8,712,127 B2 | 4/2014 | Ren et al. |
| 8,787,522 B2 | 7/2014 | Smith et al. |
| 8,897,535 B2 | 11/2014 | Ruth et al. |
| 8,983,156 B2 | 3/2015 | Periaswamy et al. |
| 9,020,579 B2 | 4/2015 | Smith |
| 9,075,903 B2 | 7/2015 | Marshall |
| 9,084,579 B2 | 7/2015 | Ren et al. |
| 9,119,599 B2 | 9/2015 | Itai |
| 9,129,362 B2 | 9/2015 | Jerebko |
| 9,289,183 B2 | 3/2016 | Karssemeijer |
| 9,451,924 B2 | 9/2016 | Bernard |
| 9,456,797 B2 | 10/2016 | Ruth et al. |
| 9,478,028 B2 | 10/2016 | Parthasarathy |
| 9,589,374 B1 | 3/2017 | Gao |
| 9,592,019 B2 | 3/2017 | Sugiyama |
| 9,805,507 B2 | 10/2017 | Chen |
| 9,808,215 B2 | 11/2017 | Ruth et al. |
| 9,811,758 B2 | 11/2017 | Ren et al. |
| 9,901,309 B2 | 2/2018 | DeFreitas et al. |
| 10,008,184 B2 | 6/2018 | Kreeger et al. |
| 10,010,302 B2 | 7/2018 | Ruth et al. |
| 10,074,199 B2 | 9/2018 | Robinson et al. |
| 10,092,358 B2 | 10/2018 | DeFreitas |
| 10,111,631 B2 | 10/2018 | Gkanatsios |
| 10,242,490 B2 | 3/2019 | Karssemeijer |
| 10,276,265 B2 | 4/2019 | Reicher et al. |
| 10,282,840 B2 | 5/2019 | Moehrle et al. |
| 10,335,094 B2 | 7/2019 | DeFreitas |
| 10,357,211 B2 | 7/2019 | Smith |
| 10,410,417 B2 | 9/2019 | Chen et al. |
| 10,413,263 B2 | 9/2019 | Ruth et al. |
| 10,444,960 B2 | 10/2019 | Marshall |
| 10,456,213 B2 | 10/2019 | DeFreitas |
| 10,573,276 B2 | 2/2020 | Kreeger et al. |
| 10,575,807 B2 | 3/2020 | Gkanatsios |
| 10,595,954 B2 | 3/2020 | DeFreitas |
| 10,624,598 B2 | 4/2020 | Chen |
| 10,977,863 B2 | 4/2021 | Chen |
| 10,978,026 B2 | 4/2021 | Kreeger |
| 11,419,565 B2 | 8/2022 | Gkanatsios |
| 11,508,340 B2 | 11/2022 | Kreeger |
| 11,701,199 B2 | 7/2023 | DeFreitas |
| 2001/0038681 A1 | 11/2001 | Stanton et al. |
| 2001/0038861 A1 | 11/2001 | Hsu et al. |
| 2002/0012450 A1 | 1/2002 | Tsuji |
| 2002/0050986 A1 | 5/2002 | Inoue |
| 2002/0075997 A1 | 6/2002 | Unger et al. |
| 2002/0113681 A1 | 8/2002 | Byram |
| 2002/0122533 A1 | 9/2002 | Marie et al. |
| 2002/0188466 A1 | 12/2002 | Barrette et al. |
| 2002/0193676 A1 | 12/2002 | Bodicker |
| 2003/0007598 A1 | 1/2003 | Wang |
| 2003/0018272 A1 | 1/2003 | Treado et al. |
| 2003/0026386 A1 | 2/2003 | Tang |
| 2003/0048260 A1 | 3/2003 | Matusis |
| 2003/0073895 A1 | 4/2003 | Nields et al. |
| 2003/0095624 A1 | 5/2003 | Eberhard et al. |
| 2003/0097055 A1 | 5/2003 | Yanof |
| 2003/0128893 A1 | 7/2003 | Castorina |
| 2003/0135115 A1 | 7/2003 | Burdette et al. |
| 2003/0169847 A1 | 9/2003 | Karellas |
| 2003/0194050 A1 | 10/2003 | Eberhard |
| 2003/0194121 A1 | 10/2003 | Eberhard et al. |
| 2003/0194124 A1 | 10/2003 | Suzuki et al. |
| 2003/0195433 A1 | 10/2003 | Turovskiy |
| 2003/0210254 A1 | 11/2003 | Doan |

(56) References Cited

U.S. PATENT DOCUMENTS

| | | |
|---|---|---|
| 2003/0212327 A1 | 11/2003 | Wang |
| 2003/0215120 A1 | 11/2003 | Uppaluri |
| 2004/0008809 A1 | 1/2004 | Webber |
| 2004/0008900 A1 | 1/2004 | Jabri et al. |
| 2004/0008901 A1 | 1/2004 | Avinash |
| 2004/0036680 A1 | 2/2004 | Davis |
| 2004/0047518 A1 | 3/2004 | Tiana |
| 2004/0052328 A1 | 3/2004 | Saboi |
| 2004/0064037 A1 | 4/2004 | Smith |
| 2004/0066884 A1 | 4/2004 | Claus |
| 2004/0066904 A1 | 4/2004 | Eberhard et al. |
| 2004/0070582 A1 | 4/2004 | Smith et al. |
| 2004/0077938 A1 | 4/2004 | Mark et al. |
| 2004/0081273 A1 | 4/2004 | Ning |
| 2004/0094167 A1 | 5/2004 | Brady |
| 2004/0101095 A1 | 5/2004 | Jing et al. |
| 2004/0109028 A1 | 6/2004 | Stern et al. |
| 2004/0109529 A1 | 6/2004 | Eberhard et al. |
| 2004/0127789 A1 | 7/2004 | Ogawa |
| 2004/0138569 A1 | 7/2004 | Grunwald |
| 2004/0171933 A1 | 9/2004 | Stoller et al. |
| 2004/0171986 A1 | 9/2004 | Tremaglio, Jr. et al. |
| 2004/0267157 A1 | 12/2004 | Miller et al. |
| 2005/0047636 A1* | 3/2005 | Gines .............. G06T 11/005 382/131 |
| 2005/0049521 A1 | 3/2005 | Miller et al. |
| 2005/0063509 A1 | 3/2005 | Defreitas et al. |
| 2005/0078797 A1 | 4/2005 | Danielsson et al. |
| 2005/0084060 A1 | 4/2005 | Seppi et al. |
| 2005/0089205 A1 | 4/2005 | Kapur |
| 2005/0105679 A1 | 5/2005 | Wu et al. |
| 2005/0107689 A1 | 5/2005 | Sasano |
| 2005/0111718 A1 | 5/2005 | MacMahon |
| 2005/0113680 A1 | 5/2005 | Ikeda et al. |
| 2005/0113681 A1 | 5/2005 | DeFreitas et al. |
| 2005/0113715 A1 | 5/2005 | Schwindt et al. |
| 2005/0124845 A1 | 6/2005 | Thomadsen et al. |
| 2005/0135555 A1 | 6/2005 | Claus |
| 2005/0135664 A1 | 6/2005 | Kaufhold |
| 2005/0226375 A1 | 10/2005 | Eberhard |
| 2006/0004278 A1 | 1/2006 | Giger et al. |
| 2006/0009693 A1 | 1/2006 | Hanover et al. |
| 2006/0018526 A1 | 1/2006 | Avinash |
| 2006/0025680 A1 | 2/2006 | Jeune-Lomme |
| 2006/0030784 A1 | 2/2006 | Miller et al. |
| 2006/0074288 A1 | 4/2006 | Kelly et al. |
| 2006/0098855 A1 | 5/2006 | Gkanatsios et al. |
| 2006/0129062 A1 | 6/2006 | Nicoson et al. |
| 2006/0132508 A1 | 6/2006 | Sadikali |
| 2006/0147099 A1 | 7/2006 | Marshall et al. |
| 2006/0154267 A1 | 7/2006 | Ma et al. |
| 2006/0155209 A1 | 7/2006 | Miller et al. |
| 2006/0197753 A1 | 9/2006 | Hotelling |
| 2006/0210131 A1 | 9/2006 | Wheeler |
| 2006/0228012 A1 | 10/2006 | Masuzawa |
| 2006/0238546 A1 | 10/2006 | Handley |
| 2006/0257009 A1 | 11/2006 | Wang |
| 2006/0269040 A1 | 11/2006 | Mertelmeier |
| 2006/0274928 A1 | 12/2006 | Collins et al. |
| 2006/0291618 A1 | 12/2006 | Eberhard et al. |
| 2007/0014468 A1* | 1/2007 | Gines .............. G06T 11/008 382/154 |
| 2007/0019846 A1 | 1/2007 | Bullitt et al. |
| 2007/0030949 A1 | 2/2007 | Jing et al. |
| 2007/0036265 A1 | 2/2007 | Jing et al. |
| 2007/0046649 A1 | 3/2007 | Reiner |
| 2007/0047793 A1 | 3/2007 | Wu et al. |
| 2007/0052700 A1 | 3/2007 | Wheeler et al. |
| 2007/0076844 A1 | 4/2007 | Defreitas et al. |
| 2007/0114424 A1 | 5/2007 | Danielsson et al. |
| 2007/0118400 A1 | 5/2007 | Morita et al. |
| 2007/0156451 A1 | 7/2007 | Gering |
| 2007/0223651 A1 | 9/2007 | Wagenaar et al. |
| 2007/0225600 A1 | 9/2007 | Weibrecht et al. |
| 2007/0236490 A1 | 10/2007 | Casteele |
| 2007/0242800 A1 | 10/2007 | Jing et al. |
| 2007/0263765 A1 | 11/2007 | Wu |
| 2007/0274585 A1 | 11/2007 | Zhang et al. |
| 2008/0019581 A1 | 1/2008 | Gkanatsios et al. |
| 2008/0043905 A1 | 2/2008 | Hassanpourgol |
| 2008/0045833 A1 | 2/2008 | DeFreitas et al. |
| 2008/0101537 A1 | 5/2008 | Sendai |
| 2008/0114614 A1 | 5/2008 | Mahesh et al. |
| 2008/0125643 A1 | 5/2008 | Huisman |
| 2008/0130979 A1 | 6/2008 | Ren |
| 2008/0139896 A1 | 6/2008 | Baumgart |
| 2008/0152086 A1 | 6/2008 | Hall |
| 2008/0165136 A1 | 7/2008 | Christie et al. |
| 2008/0187095 A1 | 8/2008 | Boone et al. |
| 2008/0198966 A1 | 8/2008 | Hjarn |
| 2008/0221479 A1 | 9/2008 | Ritchie |
| 2008/0229256 A1 | 9/2008 | Shibaike |
| 2008/0240533 A1 | 10/2008 | Piron et al. |
| 2008/0297482 A1 | 12/2008 | Weiss |
| 2009/0003519 A1 | 1/2009 | DeFreitas |
| 2009/0005668 A1 | 1/2009 | West et al. |
| 2009/0005693 A1 | 1/2009 | Brauner |
| 2009/0010384 A1 | 1/2009 | Jing et al. |
| 2009/0034684 A1 | 2/2009 | Bernard |
| 2009/0037821 A1 | 2/2009 | O'Neal et al. |
| 2009/0063118 A1 | 3/2009 | Dachille et al. |
| 2009/0079705 A1 | 3/2009 | Sizelove et al. |
| 2009/0080594 A1 | 3/2009 | Brooks et al. |
| 2009/0080602 A1 | 3/2009 | Brooks et al. |
| 2009/0080604 A1 | 3/2009 | Shores et al. |
| 2009/0080752 A1 | 3/2009 | Ruth |
| 2009/0080765 A1 | 3/2009 | Bernard et al. |
| 2009/0087067 A1 | 4/2009 | Khorasani |
| 2009/0123052 A1 | 5/2009 | Ruth |
| 2009/0129644 A1 | 5/2009 | Daw et al. |
| 2009/0135997 A1 | 5/2009 | Defreitas et al. |
| 2009/0138280 A1 | 5/2009 | Morita et al. |
| 2009/0143674 A1 | 6/2009 | Nields |
| 2009/0167702 A1 | 7/2009 | Nurmi |
| 2009/0171244 A1 | 7/2009 | Ning |
| 2009/0238424 A1 | 9/2009 | Arakita |
| 2009/0259958 A1 | 10/2009 | Ban |
| 2009/0268865 A1 | 10/2009 | Ren et al. |
| 2009/0278812 A1 | 11/2009 | Yasutake |
| 2009/0296882 A1 | 12/2009 | Gkanatsios et al. |
| 2009/0304147 A1 | 12/2009 | Jing et al. |
| 2010/0034348 A1 | 2/2010 | Yu |
| 2010/0049046 A1 | 2/2010 | Peiffer |
| 2010/0054400 A1 | 3/2010 | Ren et al. |
| 2010/0067648 A1 | 3/2010 | Kojima |
| 2010/0079405 A1 | 4/2010 | Bernstein |
| 2010/0086188 A1 | 4/2010 | Ruth et al. |
| 2010/0088346 A1 | 4/2010 | Urness et al. |
| 2010/0098214 A1 | 4/2010 | Star-Lack et al. |
| 2010/0105879 A1 | 4/2010 | Katayose et al. |
| 2010/0121178 A1 | 5/2010 | Krishnan |
| 2010/0131294 A1 | 5/2010 | Venon |
| 2010/0131482 A1 | 5/2010 | Linthicum et al. |
| 2010/0135558 A1 | 6/2010 | Ruth et al. |
| 2010/0152570 A1 | 6/2010 | Navab |
| 2010/0166147 A1 | 7/2010 | Abenaim |
| 2010/0166267 A1 | 7/2010 | Zhang |
| 2010/0171764 A1 | 7/2010 | Feng et al. |
| 2010/0189322 A1 | 7/2010 | Sakagawa |
| 2010/0195882 A1 | 8/2010 | Ren et al. |
| 2010/0208037 A1 | 8/2010 | Sendai |
| 2010/0231522 A1 | 9/2010 | Li |
| 2010/0246884 A1 | 9/2010 | Chen et al. |
| 2010/0246909 A1 | 9/2010 | Blum |
| 2010/0259561 A1 | 10/2010 | Forutanpour et al. |
| 2010/0259645 A1 | 10/2010 | Kaplan |
| 2010/0260316 A1 | 10/2010 | Stein et al. |
| 2010/0280375 A1 | 11/2010 | Zhang |
| 2010/0293500 A1 | 11/2010 | Cragun |
| 2011/0018817 A1 | 1/2011 | Kryze |
| 2011/0019891 A1 | 1/2011 | Puong |
| 2011/0054944 A1 | 3/2011 | Sandberg et al. |
| 2011/0069808 A1 | 3/2011 | Defreitas et al. |
| 2011/0069906 A1 | 3/2011 | Park |

(56) References Cited

U.S. PATENT DOCUMENTS

| | | |
|---|---|---|
| 2011/0087132 A1 | 4/2011 | DeFreitas et al. |
| 2011/0105879 A1 | 5/2011 | Masumoto |
| 2011/0109650 A1 | 5/2011 | Kreeger |
| 2011/0110570 A1 | 5/2011 | Bar-Shalev |
| 2011/0110576 A1* | 5/2011 | Kreeger ............ G06F 3/04815 |
| | | 382/132 |
| 2011/0123073 A1 | 5/2011 | Gustafson |
| 2011/0125526 A1 | 5/2011 | Gustafson |
| 2011/0134113 A1 | 6/2011 | Ma et al. |
| 2011/0150447 A1 | 6/2011 | Li |
| 2011/0157154 A1 | 6/2011 | Bernard et al. |
| 2011/0163939 A1 | 7/2011 | Tam et al. |
| 2011/0178389 A1 | 7/2011 | Kumar et al. |
| 2011/0182402 A1 | 7/2011 | Partain |
| 2011/0234630 A1 | 9/2011 | Batman et al. |
| 2011/0237927 A1 | 9/2011 | Brooks et al. |
| 2011/0242092 A1 | 10/2011 | Kashiwagi |
| 2011/0310126 A1 | 12/2011 | Georgiev et al. |
| 2012/0014501 A1* | 1/2012 | Pelc .................. A61N 5/1049 |
| | | 378/9 |
| 2012/0014504 A1 | 1/2012 | Jang |
| 2012/0014578 A1 | 1/2012 | Karssemeijer |
| 2012/0069951 A1 | 3/2012 | Toba |
| 2012/0106698 A1 | 5/2012 | Karim |
| 2012/0127297 A1* | 5/2012 | Baxi .................... G06V 20/695 |
| | | 382/173 |
| 2012/0131488 A1 | 5/2012 | Karlsson et al. |
| 2012/0133600 A1 | 5/2012 | Marshall |
| 2012/0133601 A1 | 5/2012 | Marshall |
| 2012/0134464 A1 | 5/2012 | Hoernig et al. |
| 2012/0148151 A1* | 6/2012 | Hamada ............... G06T 11/60 |
| | | 382/164 |
| 2012/0150034 A1 | 6/2012 | DeFreitas et al. |
| 2012/0189092 A1 | 7/2012 | Jerebko |
| 2012/0194425 A1 | 8/2012 | Buelow |
| 2012/0238870 A1 | 9/2012 | Smith et al. |
| 2012/0277625 A1 | 11/2012 | Nakayama |
| 2012/0293511 A1 | 11/2012 | Mertelmeier |
| 2013/0016255 A1 | 1/2013 | Bhatt |
| 2013/0022165 A1 | 1/2013 | Jang |
| 2013/0044861 A1 | 2/2013 | Muller |
| 2013/0059758 A1 | 3/2013 | Haick |
| 2013/0108138 A1 | 5/2013 | Nakayama |
| 2013/0121569 A1 | 5/2013 | Yadav |
| 2013/0121618 A1 | 5/2013 | Yadav |
| 2013/0202168 A1 | 8/2013 | Jerebko |
| 2013/0259193 A1 | 10/2013 | Packard |
| 2014/0033126 A1 | 1/2014 | Kreeger |
| 2014/0035811 A1 | 2/2014 | Guehring |
| 2014/0064444 A1 | 3/2014 | Oh |
| 2014/0073913 A1 | 3/2014 | DeFreitas et al. |
| 2014/0082542 A1 | 3/2014 | Zhang et al. |
| 2014/0200433 A1 | 7/2014 | Choi |
| 2014/0219534 A1* | 8/2014 | Wiemker .............. G06T 7/187 |
| | | 382/131 |
| 2014/0219548 A1 | 8/2014 | Wels |
| 2014/0276061 A1 | 9/2014 | Lee et al. |
| 2014/0327702 A1 | 11/2014 | Kreeger et al. |
| 2014/0328517 A1 | 11/2014 | Gluncic |
| 2015/0004558 A1* | 1/2015 | Inglese ............... A61B 6/4233 |
| | | 433/29 |
| 2015/0052471 A1 | 2/2015 | Chen |
| 2015/0061582 A1 | 4/2015 | Smith |
| 2015/0238148 A1 | 8/2015 | Georgescu |
| 2015/0258271 A1 | 9/2015 | Love |
| 2015/0302146 A1 | 10/2015 | Marshall |
| 2015/0309712 A1 | 10/2015 | Marshall |
| 2015/0317538 A1 | 11/2015 | Ren et al. |
| 2015/0331995 A1 | 11/2015 | Zhao |
| 2016/0000399 A1 | 1/2016 | Halmann et al. |
| 2016/0022364 A1 | 1/2016 | DeFreitas et al. |
| 2016/0051215 A1 | 2/2016 | Chen |
| 2016/0078645 A1 | 3/2016 | Abdurahman |
| 2016/0140749 A1 | 5/2016 | Erhard |
| 2016/0210774 A1 | 7/2016 | Wiskin et al. |
| 2016/0228034 A1 | 8/2016 | Gluncic |
| 2016/0235380 A1 | 8/2016 | Smith |
| 2016/0350933 A1 | 12/2016 | Schieke |
| 2016/0364526 A1 | 12/2016 | Reicher et al. |
| 2016/0367210 A1 | 12/2016 | Gkanatsios |
| 2017/0071562 A1 | 3/2017 | Suzuki |
| 2017/0132792 A1 | 5/2017 | Jerebko et al. |
| 2017/0202453 A1 | 7/2017 | Sekiguchi |
| 2017/0262737 A1 | 9/2017 | Rabinovich |
| 2018/0008220 A1 | 1/2018 | Boone et al. |
| 2018/0008236 A1 | 1/2018 | Venkataraman et al. |
| 2018/0047211 A1 | 2/2018 | Chen et al. |
| 2018/0109698 A1 | 4/2018 | Ramsay et al. |
| 2018/0132722 A1 | 5/2018 | Eggers et al. |
| 2018/0137385 A1 | 5/2018 | Ren |
| 2018/0144244 A1 | 5/2018 | Masoud |
| 2018/0256118 A1 | 9/2018 | DeFreitas |
| 2019/0000318 A1 | 1/2019 | Caluser |
| 2019/0015173 A1 | 1/2019 | DeFreitas |
| 2019/0037173 A1 | 1/2019 | Lee et al. |
| 2019/0043456 A1 | 2/2019 | Kreeger |
| 2019/0057778 A1 | 2/2019 | Porter et al. |
| 2019/0287241 A1 | 9/2019 | Hill et al. |
| 2019/0290221 A1 | 9/2019 | Smith |
| 2019/0325573 A1 | 10/2019 | Bernard et al. |
| 2020/0046303 A1 | 2/2020 | DeFreitas |
| 2020/0054300 A1 | 2/2020 | Kreeger et al. |
| 2020/0093562 A1 | 3/2020 | DeFreitas |
| 2020/0184262 A1 | 6/2020 | Chui |
| 2020/0205928 A1 | 7/2020 | DeFreitas |
| 2020/0253573 A1 | 8/2020 | Gkanatsios |
| 2020/0390404 A1 | 12/2020 | DeFreitas |
| 2021/0000553 A1 | 1/2021 | St. Pierre |
| 2021/0100518 A1 | 4/2021 | Chui |
| 2021/0100626 A1 | 4/2021 | St. Pierre |
| 2021/0113167 A1 | 4/2021 | Chui |
| 2021/0118199 A1 | 4/2021 | Chui |
| 2021/0174504 A1 | 6/2021 | Madabhushi |
| 2021/0212665 A1 | 7/2021 | Tsymbalenko |
| 2022/0005277 A1 | 1/2022 | Chen |
| 2022/0013089 A1 | 1/2022 | Kreeger |
| 2022/0036545 A1 | 2/2022 | St. Pierre |
| 2022/0192615 A1 | 6/2022 | Chui |
| 2022/0254023 A1 | 8/2022 | McKinney et al. |
| 2022/0386969 A1 | 12/2022 | Smith |
| 2023/0000467 A1 | 1/2023 | Shi |
| 2023/0038498 A1 | 2/2023 | Xu |
| 2023/0053489 A1 | 2/2023 | Kreeger |
| 2023/0054121 A1 | 2/2023 | Chui |
| 2023/0056692 A1 | 2/2023 | Gkanatsios |
| 2023/0082494 A1 | 3/2023 | Chui |
| 2023/0098305 A1 | 3/2023 | St. Pierre |
| 2023/0103969 A1 | 4/2023 | St. Pierre |
| 2023/0124481 A1 | 4/2023 | St. Pierre |
| 2023/0125385 A1 | 4/2023 | Solis |
| 2023/0225821 A1 | 7/2023 | DeFreitas |
| 2023/0344453 A1 | 10/2023 | Yang |
| 2024/0169958 A1 | 5/2024 | Kreeger |
| 2024/0315654 A1 | 9/2024 | Chui |
| 2024/0320827 A1 | 9/2024 | Chui |

FOREIGN PATENT DOCUMENTS

| | | |
|---|---|---|
| CN | 1846622 | 10/2006 |
| CN | 101066212 A | 11/2007 |
| CN | 102169530 A | 8/2011 |
| CN | 202161328 | 3/2012 |
| CN | 102429678 | 5/2012 |
| CN | 102473300 A | 5/2012 |
| CN | 105193447 | 12/2015 |
| CN | 106659468 A | 5/2017 |
| CN | 107440730 | 12/2017 |
| CN | 112561908 A | 3/2021 |
| DE | 102010009295 | 8/2011 |
| DE | 102011087127 | 5/2013 |
| EP | 775467 | 5/1997 |
| EP | 982001 | 3/2000 |
| EP | 1428473 | 6/2004 |

(56) References Cited

FOREIGN PATENT DOCUMENTS

| | | |
|---|---|---|
| EP | 2236085 | 6/2010 |
| EP | 2215600 | 8/2010 |
| EP | 2301432 | 3/2011 |
| EP | 2491863 | 8/2012 |
| EP | 1986548 | 1/2013 |
| EP | 2656789 | 10/2013 |
| EP | 2823464 | 1/2015 |
| EP | 2823765 | 1/2015 |
| EP | 2889743 | 7/2015 |
| EP | 3060132 | 4/2019 |
| JP | H09-35043 | 2/1997 |
| JP | H09-198490 | 7/1997 |
| JP | H09-238934 | 9/1997 |
| JP | 10-33523 | 2/1998 |
| JP | 2000-200340 | 7/2000 |
| JP | 2002-109510 | 4/2002 |
| JP | 2002-282248 | 10/2002 |
| JP | 2003-126073 | 5/2003 |
| JP | 2003-189179 | 7/2003 |
| JP | 2003-199737 | 7/2003 |
| JP | 2003-531516 | 10/2003 |
| JP | 2004254742 | 9/2004 |
| JP | 2005-110843 | 4/2005 |
| JP | 2005-522305 | 7/2005 |
| JP | 2005-227350 | 8/2005 |
| JP | 2005-322257 | 11/2005 |
| JP | 2006-519634 | 8/2006 |
| JP | 2006-312026 | 11/2006 |
| JP | 2007-130487 | 5/2007 |
| JP | 2007-216022 | 8/2007 |
| JP | 2007-325928 | 12/2007 |
| JP | 2007-330334 | 12/2007 |
| JP | 2007-536968 | 12/2007 |
| JP | 2008-068032 | 3/2008 |
| JP | 2008518684 | 6/2008 |
| JP | 2008-253401 | 10/2008 |
| JP | 2009-034503 | 2/2009 |
| JP | 2009-522005 | 6/2009 |
| JP | 2009-526618 | 7/2009 |
| JP | 2009-207545 | 9/2009 |
| JP | 2010-137004 | 6/2010 |
| JP | 2011-110175 A | 6/2011 |
| JP | 2012-501750 | 1/2012 |
| JP | 2012011255 | 1/2012 |
| JP | 2012-061196 | 3/2012 |
| JP | 2013-530768 | 8/2013 |
| JP | 2013-244211 | 12/2013 |
| JP | 2014-507250 | 3/2014 |
| JP | 2014-534042 | 12/2014 |
| JP | 2015-506794 | 3/2015 |
| JP | 2015-144632 A | 8/2015 |
| JP | 2016-198197 | 12/2015 |
| JP | 2016059743 | 4/2016 |
| JP | 2017-000364 | 1/2017 |
| JP | 2017-056358 | 3/2017 |
| KR | 10-2015-0010515 | 1/2015 |
| KR | 10-2017-0062839 | 6/2017 |
| WO | 90/05485 | 5/1990 |
| WO | 93/17620 | 9/1993 |
| WO | 94/06352 | 3/1994 |
| WO | 1997/00649 | 1/1997 |
| WO | 1998/16903 | 4/1998 |
| WO | 00/51484 | 9/2000 |
| WO | 2003/020114 | 3/2003 |
| WO | 03/077202 | 9/2003 |
| WO | 2005051197 | 6/2005 |
| WO | 2005110230 | 11/2005 |
| WO | 2005/112767 | 12/2005 |
| WO | 2006/055830 | 5/2006 |
| WO | 2006/058160 | 6/2006 |
| WO | 2007/095330 | 8/2007 |
| WO | 08/014670 | 2/2008 |
| WO | 2008047270 | 4/2008 |
| WO | 2008/050823 | 5/2008 |
| WO | 2008/054436 | 5/2008 |
| WO | 2009/026587 | 2/2009 |
| WO | 2010/028208 | 3/2010 |
| WO | 2010059920 | 5/2010 |
| WO | 2011008239 | 1/2011 |
| WO | 2011/043838 | 4/2011 |
| WO | 2011065950 | 6/2011 |
| WO | 2011073864 | 6/2011 |
| WO | 2011091300 | 7/2011 |
| WO | 2012/001572 | 1/2012 |
| WO | 2012/068373 | 5/2012 |
| WO | 2012063653 | 5/2012 |
| WO | 2012/112627 | 8/2012 |
| WO | 2012/122399 | 9/2012 |
| WO | 2013/001439 | 1/2013 |
| WO | WO 2013/035026 | 3/2013 |
| WO | 2013/078476 | 5/2013 |
| WO | 2013/123091 | 8/2013 |
| WO | 2013/136222 | 9/2013 |
| WO | 2014/080215 | 5/2014 |
| WO | WO 2014/149554 | 9/2014 |
| WO | 2014/207080 | 12/2014 |
| WO | 2015/061582 | 4/2015 |
| WO | 2015/066650 | 5/2015 |
| WO | 2015/130916 | 9/2015 |
| WO | 2016/103094 | 6/2016 |
| WO | 2016/184746 | 11/2016 |
| WO | 2016/206942 | 12/2016 |
| WO | 2018/183548 | 10/2018 |
| WO | 2018/183549 | 10/2018 |
| WO | 2018/183550 | 10/2018 |
| WO | 2018/236565 | 12/2018 |
| WO | 2019/032558 | 2/2019 |
| WO | 2019/091807 | 5/2019 |
| WO | 2021/021329 | 2/2021 |
| WO | 2021/168281 | 8/2021 |
| WO | 2021/195084 | 9/2021 |

OTHER PUBLICATIONS

Response to Rule 161(1) and 162 communication filed on Jun. 6, 2016 for European Patent Application No. 14711087.8, 14 pages.
EPO office action dated Feb. 5, 2018 for European Patent Application No. 14711087.8, 4 pages.
Response to EPO office action filed on Aug. 9, 2018 for European Patent Application No. 14711087.8, 6 pages.
Chinese office action dated Mar. 1, 2018 for Chinese Patent Application No. 201480014655.2, in Chinese with English translation provided by Chinese associate, 18 pages.
Chinese office action dated Sep. 18, 2018 for Chinese Patent Application No. 201480014655.2, in Chinese with English translation provided by Chinese associate, 27 pages.
Chinese office action dated Apr. 16, 2019 for Chinese Patent Application No. 201480014655.2, in Chinese with English translation provided by Chinese associate, 27 pages.
First office action for Japanese Application No. 2016-200514 mailed Dec. 11, 2017, including English translation provided by foreign associate, 12 pages.
Response to first office action filed Mar. 12, 2018 for Japanese Application No. 2016-200514, including English translation provided by foreign associate, 41 pages.
Response to third office action filed on Sep. 2, 2019 for Chinese Application No. 201480014655.2, in Chinese with partial translation provided by foreign associate, 23 pages.
Notification of the International Preliminary Report on Patentability mailed Sep. 24, 2015 for PCT/US2014/019515, 8 pages.
eFilm Mobile HD by Merge Healthcare, web site: http://itunes.apple.com/bw/app/efilm-mobile-hd/id405261243?mt=8, accessed on Nov. 3, 2011 (2 pages).
eFilm Solutions, eFilm Workstation (tm) 3.4, website: http://estore.merge.com/na/estore/content.aspx?productID=405, accessed on Nov. 3, 2011 (2 pages).
Wodajo, Felasfa, MD, "Now Playing: Radiology Images from Your Hospital PACS on your iPad," Mar. 17, 2010; web site: http://www.imedicalapps.com/2010/03/now-playing-radiology-images-from-your-hospital-pacs-on-your-ipad/, accessed on Nov. 3, 2011 (3 pages).

(56) References Cited

OTHER PUBLICATIONS

Giger et al. "Development of a smart workstation for use in mammography", in Proceedings of SPIE, vol. 1445 (1991), pp. 101103; 4 pages.
Giger et al., "An Intelligent Workstation for Computer-aided Diagnosis", in RadioGraphics, May 1993, 13:3 pp. 647-656; 10 pages.
Lewin, JM, et al., Dual-energy contrast-enhanced digital subtraction mammography: feasibility. Radiology 2003; 229:261-268.
Berg, WA et al., "Combined screening with ultrasound and mammography vs mammography alone in women at elevated risk of breast cancer", JAMA 299:2151-2163, 2008.
Carton, AK, et al., "Dual-energy contrast-enhanced digital breast tomosynthesis—a feasibility study", Br J Radiol. Apr. 2010;83 (988):344-50.
Chen, SC, et al., "Initial clinical experience with contrast-enhanced digital breast tomosynthesis", Acad Radio. Feb. 2007 14(2):229-38.
Diekmann, F., et al., "Digital mammography using iodine-based contrast media: initial clinical experience with dynamic contrast medium enhancement", Invest Radiol 2005; 40:397-404.
Dromain C., et al., "Contrast enhanced spectral mammography: a multi-reader study", RSNA 2010, 96th Scientific Assembly and Scientific Meeting.
Dromain, C., et al., "Contrast-enhanced digital mammography", Eur J Radiol. 2009; 69:34-42.
Freiherr, G., "Breast tomosynthesis trials show promise", Diagnostic Imaging—San Francisco 2005, V27; N4:42-48.
ICRP Publication 60: 1990 Recommendations of the International Commission on Radiological Protection, 12 pages.
Jochelson, M., et al., "Bilateral Dual Energy contrast-enhanced digital mammography: Initial Experience", RSNA 2010, 96th Scientific Assembly and Scientific Meeting, 1 page.
Jong, RA, et al., Contrast-enhanced digital mammography: initial clinical experience. Radiology 2003; 228:842-850.
Kopans, et al. Will tomosynthesis replace conventional mammography? Plenary Session SFN08: RSNA 2005.
Lehman, CD, et al. MRI evaluation of the contralateral breast in women with recently diagnosed breast cancer. N Engl J Med 2007; 356:1295-1303.
Lindfors, KK, et al., Dedicated breast CT: initial clinical experience. Radiology 2008; 246(3): 725-733.
Niklason, L., et al., Digital tomosynthesis in breast imaging. Radiology. Nov. 1997; 205(2):399-406.
Poplack, SP, et al., Digital breast tomosynthesis: initial experience in 98 women with abnormal digital screening mammography. AJR Am J Roentgenology Sep. 2007 189(3):616-23.
Prionas, ND, et al., Contrast-enhanced dedicated breast CT: initial clinical experience. Radiology. Sep. 2010 256(3):714-723.
Rafferty, E. et al., "Assessing Radiologist Performance Using Combined Full-Field Digital Mammography and Breast Tomosynthesis Versus Full-Field Digital Mammography Alone: Results" . . . presented at 2007 Radiological Society of North America meeting, Chicago IL.
Smith, A., "Full field breast tomosynthesis", Radiol Manage. Sep.-Oct. 2005; 27(5):25-31.
Weidner N, et al., "Tumor angiogenesis and metastasis: correlation in invasive breast carcinoma", New England Journal of Medicine 1991; 324:1-8.
Weidner, N, "The importance of tumor angiogenesis: the evidence continues to grow", Am J Clin Pathol. Nov. 2004 122(5):696-703.
Hologic, Inc., 510(k) Summary, prepared Nov. 28, 2010, for Affirm Breast Biopsy Guidance System Special 510(k) Premarket Notification, 5 pages.
Hologic, Inc., 510(k) Summary, prepared Aug. 14, 2012, for Affirm Breast Biopsy Guidance System Special 510(k) Premarket Notification, 5 pages.
"Filtered Back Projection", (NYGREN), published May 8, 2007, URL: http://web.archive.org/web/19991010131715/http://www.owlnet.rice.edu/~elec539/Projects97/cult/node2.html, 2 pgs.
Hologic, "Lorad StereoLoc II" Operator's Manual 9-500-0261, Rev. 005, 2004, 78 pgs.
Shrading, Simone et al., "Digital Breast Tomosynthesis-guided Vacuum-assisted Breast Biopsy: Initial Experiences and Comparison with Prone Stereotactic Vacuum-assisted Biopsy", the Department of Diagnostic and Interventional Radiology, Univ. of Aachen, Germany, published Nov. 12, 2014, 10 pgs.
"Supersonic to feature Aixplorer Ultimate at ECR", AuntiMinnie. com, 3 pages (Feb. 2018).
Bushberg, Jerrold et al., "The Essential Physics of Medical Imaging", 3rd ed., In: "The Essential Physics of Medical Imaging, Third Edition", Dec. 28, 2011, Lippincott & Wilkins, Philadelphia, PA, USA, XP05579051, pp. 270-272.
Dromain, Clarisse et al., "Dual-energy contrast-enhanced digital mammography: initial clinical results", European Radiology, Sep. 14, 2010, vol. 21, pp. 565-574.
Reynolds, April, "Stereotactic Breast Biopsy: A Review", Radiologic Technology, vol. 80, No. 5, Jun. 1, 2009, pp. 447M-464M, XP055790574.
E. Shaw de Paredes et al., "Interventional Breast Procedure", published Sep./Oct. 1998 in Curr Probl Diagn Radiol, pp. 138-184. (D15 in oppo).
Burbank, Fred, "Stereotactic Breast Biopsy: Its History, Its Present, and Its Future", published in 1996 at the Southeastern Surgical Congress, 24 pages.
Georgian-Smith, Dianne, et al., "Stereotactic Biopsy of the Breast Using an Upright Unit, a Vacuum-Suction Needle, and a Lateral Arm-Support System", 2001, at the American Roentgen Ray Society meeting, 8 pages.
Fischer Imaging Corp, Mammotest Plus manual on minimally invasive breast biopsy system, 2002, 8 pages.
Fischer Imaging Corporation, Installation Manual, MammoTest Family of Breast Biopsy Systems, 86683G, 86684G, P-55957-IM, Issue 1, Revision 3, Jul. 2005, 98 pages.
Fischer Imaging Corporation, Operator Manual, MammoTest Family of Breast Biopsy Systems, 86683G, 86684G, P-55956-OM, Issue 1, Revision 6, Sep. 2005, 258 pages.
Koechli, Ossi R., "Available Sterotactic Systems for Breast Biopsy", Renzo Brun del Re (Ed.), Minimally Invasive Breast Biopsies, Recent Results in Cancer Research 173:105-113; Springer-Verlag, 2009.
Al Sallab et al., "Self Learning Machines Using Deep Networks", Soft Computing and Pattern Recognition (SoCPaR), 2011 Int'l. Conference of IEEE, Oct. 14, 2011, pp. 21-26.
Caroline, B.E et al., "Computer aided detection of masses in digital breast tomosynthesis: A review", 2012 International Conference on Emerging Trends in Science, Engineering and Technology (INCOSET), Tiruchirappalli, 2012, pp. 186-191.
Chan, Heang-Ping et al., "ROC Study of the effect of stereoscopic imaging on assessment of breast lesions," Medical Physics, vol. 32, No. 4, Apr. 2005, 1001-1009.
Ertas, M. et al., "2D versus 3D total variation minimization in digital breast tomosynthesis", 2015 IEEE International Conference on Imaging Systems and Techniques (IST), Macau, 2015, pp. 1-4.
Ghiassi, M. et al., "A Dynamic Architecture for Artificial Networks", Neurocomputing, vol. 63, Aug. 20, 2004, pp. 397-413.
Lilja, Mikko, "Fast and accurate voxel projection technique in free-form cone-beam geometry with application to algebraic reconstruction," Applies Sciences on Biomedical and Communication Technologies, 2008, Isabel '08, first international symposium on, IEEE, Piscataway, NJ, Oct. 25, 2008.
Pathmanathan et al., "Predicting tumour location by simulating large deformations of the breast using a 3D finite element model and nonlinear elasticity", Medical Image Computing and Computer-Assisted Intervention, pp. 217-224, vol. 3217 (2004).
Pediconi, "Color-coded automated signal intensity-curve for detection and characterization of breast lesions: Preliminary evaluation of new software for MR-based breast imaging," International Congress Series 1281 (2005) 1081-1086.
Sakic et al., "Mammogram synthesis using a 3D simulation. I. breast tissue model and image acquisition simulation" Medical Physics. 29, pp. 2131-2139 (2002).
Samani, A. et al., "Biomechanical 3-D Finite Element Modeling of the Human Breast Using MRI Data", 2001, IEEE Transactions on Medical Imaging, vol. 20, No. 4, pp. 271-279.

(56) References Cited

OTHER PUBLICATIONS

Yin, H.M., et al., "Image Parser: a tool for finite element generation from three-dimensional medical images", BioMedical Engineering Online. 3:31, pp. 1-9, Oct. 1, 2004.
Van Schie, Guido, et al., "Mass detection in reconstructed digital breast tomosynthesis vols. with a computer-aided detection system trained on 2D mammograms", Med. Phys. 40(4), Apr. 2013, 41902-1-41902-11.
Van Schie, Guido, et al., "Generating Synthetic Mammograms from Reconstructed Tomosynthesis Volumes", IEEE Transactions on Medical Imaging, vol. 32, No. 12, Dec. 2013, 2322-2331.
Diekmann, Felix et al., "Thick Slices from Tomosynthesis Data Sets: Phantom Study for the Evaluation of Different Algorithms", Journal of Digital Imaging, Springer, vol. 22, No. 5, Oct. 23, 2007, pp. 519-526.
Conner, Peter, "Breast Response to Menopausal Hormone Therapy—Aspects on Proliferation, apoptosis and Mammographic Density", 2007 Annals of Medicine, 39;1, 28-41.
Glick, Stephen J., "Breast CT", Annual Rev. Biomed. Eng., 2007, 9;501-26.
Metheany, Kathrine G. et al., "Characterizing anatomical variability in breast CT images", Oct. 2008, Med. Phys. 35 (10); 4685-4694.
Dromain, Clarisse, et al., "Evaluation of tumor angiogenesis of breast carcinoma using contrast-enhanced digital mammography", AJR: 187, Nov. 2006, 16 pages.
Zhao, Bo, et al., "Imaging performance of an amorphous selenium digital mammography detector in a breast tomosynthesis system", May 2008, Med. Phys 35(5); 1978-1987.
Mahesh, Mahadevappa, "AAPM/RSNA Physics Tutorial for Residents—Digital Mammography: An Overview", Nov.-Dec. 2004, vol. 24, No. 6, 1747-1760.
Zhang, Yiheng et al., "A comparative study of limited-angle cone-beam reconstruction methods for breast tomosythnesis", Med Phys., Oct. 2006, 33(10): 3781-3795.
Sechopoulos, et al., "Glandular radiation dose in tomosynthesis of the breast using tungsten targets", Journal of Applied Clinical Medical Physics, vol. 8, No. 4, Fall 2008, 161-171.
Wen, Junhai et al., "A study on truncated cone-beam sampling strategies for 3D mammography", 2004, IEEE, 3200-3204.
Ijaz, Umer Zeeshan, et al., "Mammography phantom studies using 3D electrical impedance tomography with numerical forward solver", Frontiers in the Convergence of Bioscience and Information Technologies 2007, 379-383.
Kao, Tzu-Jen et al., "Regional admittivity spectra with tomosynthesis images for breast cancer detection", Proc. Of the 29th Annual Int'l. Conf. of the IEEE EMBS, Aug. 23-26, 2007, 4142-4145.
Varjonen, Mari, "Three-Dimensional Digital Breast Tomosynthesis in the Early Diagnosis and Detection of Breast Cancer", IWDM 2006, LNCS 4046, 152-159.
Taghibakhsh, f. et al., "High dynamic range 2-TFT amplified pixel sensor architecture for digital mammography tomosynthesis", IET Circuits Devices Syst., 2007, 1(10, pp. 87-92.
Chan, Heang-Ping et al., "Computer-aided detection system for breast masses on digital tomosynthesis mammograms: Preliminary Experience", Radiology, Dec. 2005, 1075-1080.
Kopans, Daniel B., "Breast Imaging", 3rd Edition, Lippincott Williams and Wilkins, published Nov. 2, 2006, pp. 960-967.
Williams, Mark B. et al., "Optimization of exposure parameters in full field digital mammography", Medical Physics 35, 2414 (May 20, 2008); doi: 10.1118/1.2912177, pp. 2414-2423.
Elbakri, Idris A. et al., "Automatic exposure control for a slot scanning full field digital mammography system", Med. Phys. Sep. 2005; 32(9): 2763-2770, Abstract only.
Feng, Steve Si Jia, et al., "Clinical digital breast tomosynthesis system: Dosimetric Characterization", Radiology, Apr. 2012, 263(1); pp. 35-42.
Duan, Xiaoman et al., "Matching corresponding regions of interest on cranio-caudal and medio-lateral oblique view mammograms", IEEE Access, vol. 7, Mar. 25, 2019, pp. 31586-31597, XP011715754, DOI: 10.1109/Access.2019.2902854, retrieved on Mar. 20, 2019, abstract.
Samulski, Maurice et al., "Optimizing case-based detection performance in a multiview CAD system for mammography", IEEE Transactions on Medical Imaging, vol. 30, No. 4, Apr. 1, 2011, pp. 1001-1009, XP011352387, ISSN: 0278-0062, DOI: 10.1109/TMI.2011.2105886, abstract.
Nikunjc, Oza et al., Dietterich, T.G., Ed., "Ensemble methods in machine learning", Jan. 1, 2005, Multiple Classifier Systems, Lecture Notes in Computer Science; LNCS, Springer-Verlag Berlin/Heidelberg, pp. 1-15, abstract.
Cho, N. et al., "Distinguishing Benign from Malignant Masses at Breast US: Combined US Elastography and Color Doppler US-Influence on Radiologist Accuracy", Radiology, 262(1): 80-90 (Jan. 2012).
Green, C. et al., "Deformable mapping using biochemical models to relate corresponding lesions in digital breast tomosynthesis and automated breast ultrasound images", Medical Image Analysis, 60: 1-18 (Nov. 2019).
Kim, Eun Sil, et al., "Significance of microvascular evaluation of ductal lesions on breast ultrasonography: Influence on diagnostic performance", Clinical Imaging, Elsevier, NY, vol. 51, Jun. 6, 2018, pp. 252-259.
Lee, E. et al., "Combination of Quantitative Parameters of Shear Wave Elastography and Superb Microvascular Imaging to Evaluate Breast Masses", Korean Journal of Radiology: Official Journal of the Korean Radiological Society, 21(9): 1045-1054 (Jan. 2020).
Love, Susan M., et al. "Anatomy of the nipple and breast ducts revisited", Cancer, American Cancer Society, Philadelphia, PA, vol. 101, No. 9, Sep. 20, 2004, pp. 1947-1957.

\* cited by examiner

SYSTEM AND METHOD FOR NAVIGATING A TOMOSYNTHESIS STACK INCLUDING AUTOMATIC FOCUSING

RELATED APPLICATION DATA

The present application is a continuation of U.S. Pat. No. 10,624,598, filed Aug. 31, 2015, which is a National Phase entry under 35 U.S.C § 371 of International Patent Application No. PCT/US2014/019515, having an international filing date of Feb. 28, 2014, which claims the benefit under 35 U.S.C. § 119 to U.S. Provisional Patent Application Ser. No. 61/793,437, filed Mar. 15, 2013, which is incorporated by reference in its entirety into the present application.

FIELD

The inventions disclosed herein pertain to breast imaging using tomosynthesis, and more specifically to a system and method that employs automated focusing capabilities for guiding the navigation of a tomosynthesis data set.

BACKGROUND

Mammography has long been used to screen for breast cancer and other abnormalities. Traditionally, mammograms have been formed on x-ray film. More recently, flat panel digital imagers have been introduced that acquire a mammogram in digital form, and thereby facilitate analysis and storage of the acquired images, and provide other benefits as well. Further, substantial attention and technological development has been dedicated towards obtaining three-dimensional images of the breast, using methods such as breast tomosynthesis. In contrast to the 2D images generated by legacy mammography systems, breast tomosynthesis systems construct a 3D image volume from a series of 2D projection images, each projection image obtained at a different angular displacement of an x-ray source relative to the image detector as the x-ray source is scanned over the detector. The constructed 3D image volume is typically presented as a plurality of slices of image data, the slices often being geometrically reconstructed on planes parallel to the paddle, although other reconstruction angles are possible. The reconstructed tomosynthesis slices reduce or eliminate the problems caused by tissue overlap and structure noise present in single projection 2D mammography imaging, by permitting a reviewer (e.g., a radiologist or other medical professional) to scroll through the image slices to view underlying structures.

Tomosynthesis systems have recently been developed for breast cancer screening and diagnosis. In particular, Hologic, Inc. (www.hologic.com), has developed a fused, multimode mammography/tomosynthesis system that acquires one or both types of mammogram and tomosynthesis images, either while the breast remains immobilized or in different compressions of the breast. Other companies have proposed the introduction of systems which are dedicated to tomosynthesis imaging only, i.e., which do not include the ability to also acquire a 2D mammogram.

However, systems restricted to tomosynthesis acquisition and image display are slow to gain acceptance as a replacement for conventional 2D mammogram images. In particular, conventional 2D mammograms provide good visualization of micro-calcifications, and can offer higher spatial resolution, when compared with tomosynthesis images. While tomosynthesis images provided by dedicated breast tomosynthesis systems have many desirable characteristics, e.g., better isolation and visualization of structures in the breast, such systems do not necessarily leverage existing image interpretation expertise.

In particular, because of the limited angle employed during tomosynthesis image acquisition, a breast structure would normally be visible on multiple tomosynthesis reconstructed image slices. However, it is only near the actual "depth" (location along the z-axis of the tomosynthesis images) where the breast structure is actually located that the image slices for that structure will provide sharp margin/contour/detail of the structure, i.e., as if the structure/object is "in-focus"; whereas on other slices, the structure/object may be visible but associated with fuzzy margin/contour/detail, i.e., as if the structure/object is "out-of-focus." Further, it is possible that some objects or regions of interest will only be recognizable in image slices that are reasonably close to the actual object/structure depth. As such, a reviewer may need to expend a relatively significant amount of time navigating through the images of the entire breast tomosynthesis stack, which can typically include 40-100 images, or more, depending on the breast size and reconstruction slice thickness, in order to locate a "best focus" image of an object or region of clinical interest for purposes of evaluation. This additional time needed to review a tomosynthesis stack can detour the reviewer from otherwise taking full advantage of the additional benefits provided by detailed tomosynthesis image slices over a traditional mammogram, especially when given the limited amount of time typically allocated for the review.

Thus, it would be of particular benefit to provide a system and methods for providing the reviewer with the ability to quickly and accurately locate an image or subset of images having a best focus of an object or region of interest in a tomosynthesis stack.

SUMMARY

According to one aspect of the inventions disclosed and described herein, a computer-controlled workstation is provided for navigating and reviewing a tomosynthesis image data set, the data set comprising volumetric image data of a breast, wherein the workstation is configured to display an image or a series of images from the data set on a display monitor operatively associated with the workstation, and wherein a reviewer may select or otherwise indicate through a user interface of the system an object or region of interest in a presently displayed image of the data set, thereby causing to be automatically displayed on the display monitor an image from the data set having a best focus measure of the user selected or indicated object or region of interest. Additionally and/or alternatively, in response to a detected user selection or indication of an object or region of interest in a then-displayed image from the data set, the system displays a series of near-focus images from the data set, the series comprising images having computed focus measure values within a predetermined range of, and including, a best focus measure value computed for any image of the data set depicting the user selected or indicated object or region of interest. In either case, if the then-displayed image comprises the image having the best focus of the user selected or indicated object or region of interest, the workstation may provide a visual or audible signal to the user.

In particular, because of the limited angle employed during tomosynthesis image acquisition, a breast structure would normally be visible on multiple tomosynthesis reconstructed image slices. However, it is only near the actual "depth" (location along the z-axis of the tomosynthesis images) that the breast structure is actually located that the image slices for that structure will provide sharp margin/contour/detail of the structure, i.e., as if the structure/object is "in-focus"; whereas on other slices, the structure/object may be visible but associated with fuzzy margin/contour/detail, i.e., as if the structure/object is "out-of-focus." Further, it is possible that some objects or regions of interest will only be recognizable in image slices that are reasonably close to the actual object/structure depth. As such, without the advantages provided by the inventions disclosed herein, a reviewer may need to expend a relatively significant amount of time navigating through the images of an entire breast tomosynthesis stack, which can typically include 40-100 images, or even more, depending on the breast size and reconstruction slice thickness, in order to locate a "best focus" image of an object or region of clinical interest for purposes of evaluation. Thus, it is of particular benefit of the disclosed inventions to provide a system and methods for providing the reviewer with the ability to quickly and accurately locate an image or subset of images having a "best focus" of an object or region of interest in a tomosynthesis stack.

In various embodiments of the disclosed invention, the image having a best focus measure of the user selected or indicated object or region of interest is determined based on a comparison of a focus measure of the object or region of interest computed for each image of the data set. By way of non-limiting examples, the focus measure may be computed based upon a sharpness of detected edges of the object or region of interest, a contrast of the object or region of interest, or a ratio between a measured magnitude of one or more high frequency components and a measured magnitude of one or more low frequency components. It follows that a subset of near-focus images may be identified based on their proximity in the tomosynthesis stack, i.e., along the z-axis of the images, to the image having a highest focus measure.

In some embodiments, the user selected or indicated object or region of interest may be highlighted in the displayed image having a best focus thereof. For example, the user selected or indicated object or region of interest may be highlighted by a contour line representing a boundary of the highlighted object or region. Additionally and/or alternatively, the user selected or indicated object or region of interest is highlighted in a manner indicating that the highlighted object or region is or includes a specified type of tissue structure.

In embodiments in which the system displays a series of near-focus images in response to detecting a user selection or indication of an object or region of interest, the series of near-focus images may be displayed simultaneously, i.e., in a particular order, so as to allow for a static review and comparison of the user selected or indicated object or region of interest in each image. Alternatively and/or additionally, the series of near-focus images may be displayed in succession, so as to allow for a dynamic review and comparison of the user selected or indicated object or region of interest in each image. For example, the parameters for the selection and displaying of the series near-focus images may be configurable through the user interface. In one embodiment, the series of near-focus images are displayed one-by-one, starting from a farthest from focused image, and thereafter continually approaching, and (optionally) ending with, the best focus image. Once the best focus image is reached, instead of ending the display sequence, the system may (e.g., based on a user preference) display the next adjacent near focus images, up to a certain range, then come back to the best focus image, thereby allowing the user to get a good perspective of all the images surrounding the best focus image.

In accordance with another embodiment of the disclosed inventions, an automated method employing a computer-controlled workstation is provided for navigating and displaying breast tissue images, the workstation comprising an operatively associated user interface and display monitor, the method comprising: obtaining a tomosynthesis image data set, the data set comprising volumetric image data of a breast; displaying a series of images from the data set on the display monitor in response to one or more user commands received through the user interface; detecting through the user interface a user selection or indication of an object or region of interest in a then-displayed image from the data set; highlighting the user selected or indicated object or region of interest in the then-displayed image with a visual indicia; and as further images of the series are displayed, continuing to highlight the user selected or indicated object or region of interest, while modifying the visual indicia.

The visual indicia may be a geometric shape, wherein modifying the visual indicia comprises changing a size of the geometric shape according to a relative focus measure of the user selected or indicated object or region of interest in a currently displayed image. Alternatively, the visual indicia may be a color, wherein modifying the visual indicia comprises changing a hue of the color according to a relative focus measure of the user selected or indicated object or region of interest in a currently displayed image.

These and other aspects and embodiments of the disclosed inventions are described in more detail below, in conjunction with the accompanying figures.

DETAILED DESCRIPTION OF THE ILLUSTRATED EMBODIMENTS

In describing the depicted embodiments of the disclosed inventions illustrated in the accompanying figures, specific terminology is employed for the sake of clarity and ease of description. However, the disclosure of this patent specification is not intended to be limited to the specific terminology so selected, and it is to be understood that each specific element includes all technical equivalents that operate in a similar manner. It is to be further understood that the various elements and/or features of different illustrative embodiments may be combined with each other and/or substituted for each other wherever possible within the scope of this disclosure and the appended claims.

Tomosynthesis Imaging Acquisition and Computation

Figure 1:
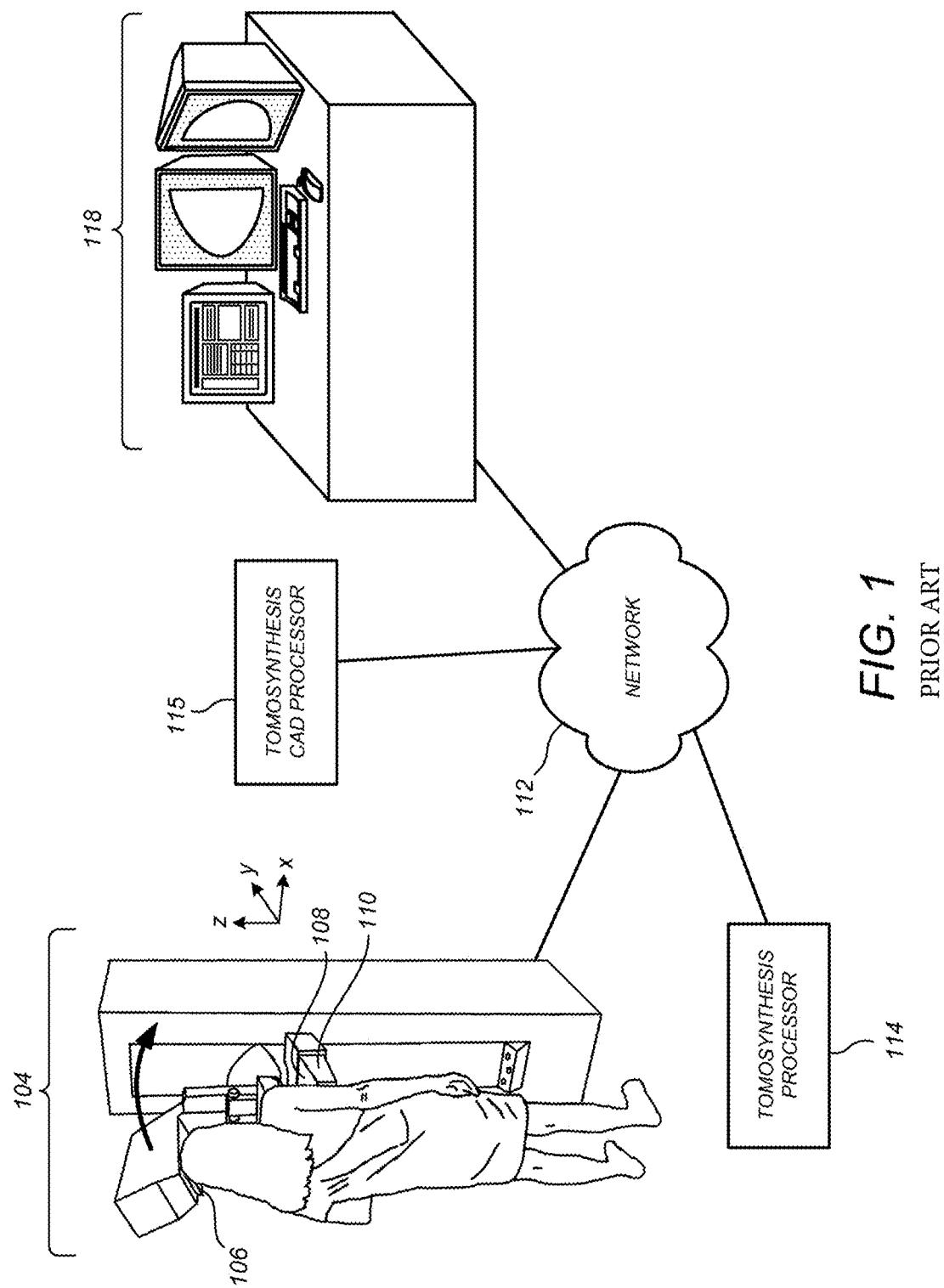
FIG. 1 illustrates a conceptual diagram of a breast x-ray tomosynthesis imaging environment, including a tomosynthesis CAD processor.
Figure 2:
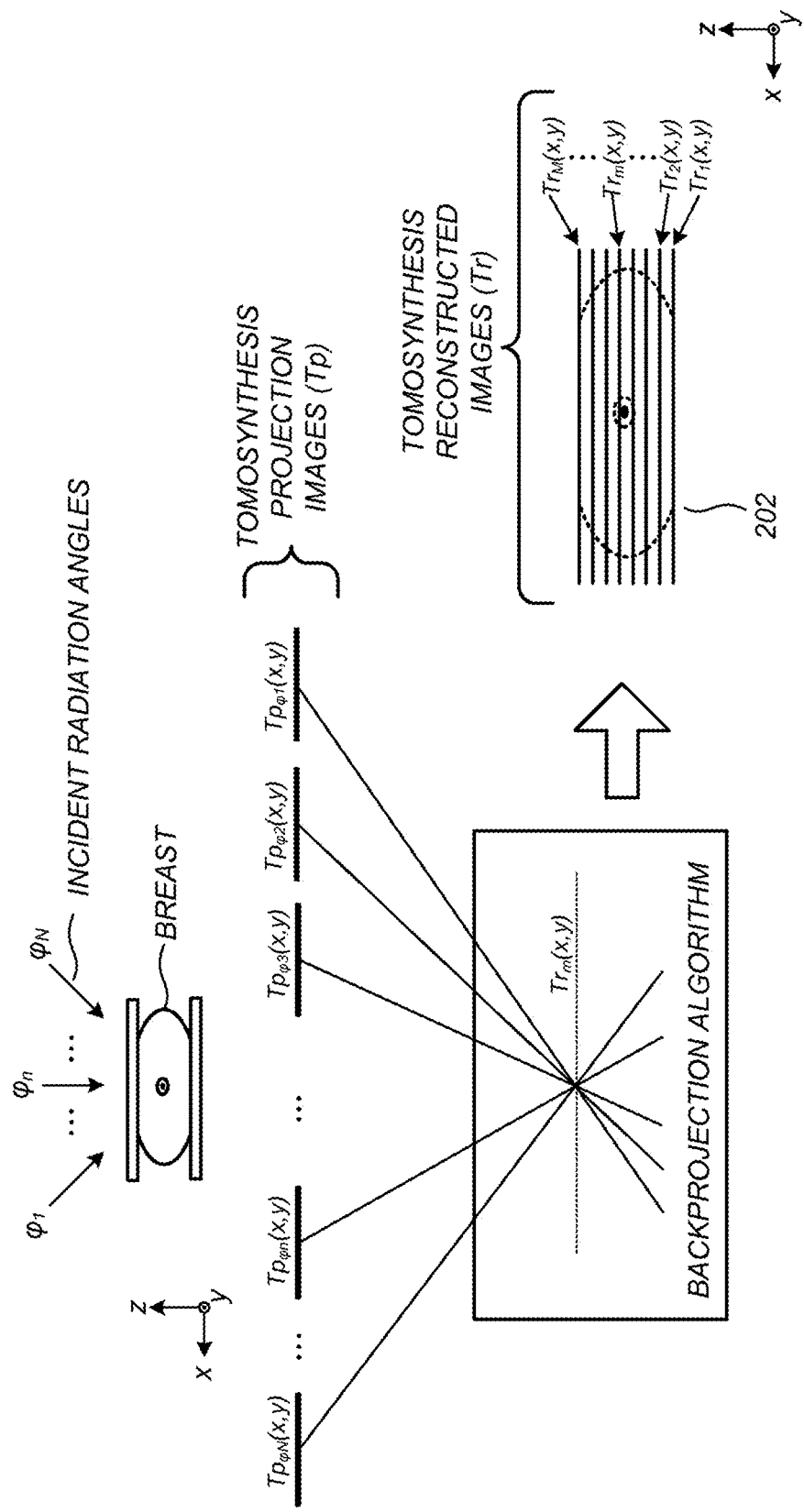
FIG. 2 illustrates exemplary breast x-ray tomosynthesis projection and reconstruction geometries.

In order to provide additional background information, reference is made to FIG. 1 and FIG. 2 taken from U.S. Pat. No. 8,223,916, entitled "Computer-aided detection of anatomical abnormalities in x-ray tomosynthesis images," which is incorporated herein by reference in its entirety.

FIG. 1 illustrates a conceptual diagram of a breast x-ray tomosynthesis imaging environment, including Computer Aided Detection (CAD) capability. Shown in FIG. 1 is a network 112, which may be a HIS/RIS (Hospital Information System/Radiology Information System) network, to which is coupled a breast x-ray tomosynthesis acquisition device 104. The acquisition device 104 includes an x-ray source 106 projecting x-rays toward a woman's breast that is supported on a breast platform 108, along with an x-ray imager 110 underlying the breast platform 108. The x-ray source 106 is moved in an arcuate path relative to the breast platform 108 and emits x-ray radiation at specified angles therealong which are captured by the x-ray imager 110 to form a set of tomosynthesis projection images. The tomosynthesis projection images are processed by a tomosynthesis processor 114 according to one or more tomosynthesis reconstruction algorithms to form tomosynthesis reconstructed images, these images being formed and filtered with a view toward optimal visual display to a radiologist ("for presentation"). In a separate process, the tomosynthesis projection images are processed by a tomosynthesis CAD processor 115 to detect anatomical abnormalities in the breast volume. The tomosynthesis image information is then viewed in conjunction with the associated CAD results at a radiology review workstation 118.

FIG. 2 illustrates a conceptual diagram of breast x-ray tomosynthesis projection imaging at different angles. Incident radiation impinges upon a compressed breast volume at a plurality "N" of breast x-ray tomosynthesis projection angles $\varphi_n$, n=1 . . . N, to result in a corresponding plurality "N" of tomosynthesis projection images $Tp_{\varphi_n}(x,y)$, n=1 . . . N. In typical scenarios, there can be N=11 or N=15 projection images, each projection image $Tp_{\varphi_n}(x,y)$ containing roughly 1710×2140 pixels, which would correspond to an x-ray detector that is roughly 24 cm×30 cm in size having a pixel resolution of 140 μm.

Also illustrated in FIG. 2 is a three-dimensional geometry 202 for the imaged breast volume, along with a conceptual icon of a tomosynthesis reconstruction algorithm in which, for a particular plane "m" having a predetermined height $h_m$ above the detection plane, the "N" projection images $Tp_{\varphi_n}(x,y)$, n=1 . . . N, are processed into a two-dimensional tomosynthesis reconstructed image $Tr_m(x,y)$. More specifically, the N projection images $Tp_{\varphi_n}(x,y)$, n=1 . . . N are combined by backprojection (or other tomosynthesis reconstruction algorithm) to form the tomosynthesis reconstructed image $Tr_m(x,y)$ based on that specific value of $h_m$ in a manner that highlights (e.g., does not blur) the effects of x-ray attenuating tissues located near that predetermined height $h_m$ and that de-emphasizes (e.g., blurs) x-ray attenuating tissues located away from that predetermined height $h_m$.

In theory, the number of different predetermined heights $h_m$ for which distinct two-dimensional tomosynthesis reconstructed images $Tr_m(x,y)$ can be generated is arbitrarily large, because $h_m$ is simply a selectable parameter fed to the reconstruction (backprojection) algorithm. In practice, because the ultimate amount of useful information is limited by the finite count of "N" projection images, the tomosynthesis reconstruction geometry is usually limited to a predetermined number "M" of reconstructed image arrays $Tr_m(x,y)$. Preferably, the number "M" is selected such that the reconstructed image arrays $Tr_m(x,y)$ uniformly fill out the vertical extent of the imaged breast volume between the lower and upper compression plates, at a vertical spacing (such as 1 mm) that is small enough to capture smaller-sized micro-calcifications.

The lateral extent of each tomosynthesis reconstruction image $Tr_m(x,y)$, can be similar to that of each projection image $Tp_{\varphi_n}(x,y)$, i.e., the number of pixels and the spatial resolution of the tomosynthesis reconstructed images $Tr_m(x,y)$ can be similar as for the projection images $Tp_{\varphi_n}(x,y)$. However, such correspondence is not required, with supersampling, subsampling, or other resampling being available for various reasons. For example, the particular geometries of different tomosynthesis reconstruction algorithms could be different from each other, in which case such resampling is incorporated therein as needed to cause the resultant arrays that will be being compared, added, multiplied, mapped, or otherwise jointly processed to be in registration with each other. Depending on the particular tomosynthesis reconstruction algorithm being used, the lateral resolution of the different tomosynthesis reconstructed images $Tr_m(x,y)$ can be different for different levels, for example, the uppermost level could be 95 μm per pixel while the lowermost level be 108 μm per pixel.

As used herein, three-dimensional geometry of the imaged breast volume refers to a space-limited three-dimensional grid having a defined number of levels that extends at least throughout a clinically relevant portion of the breast (for example, including the breast parenchyma but excluding the skin and the empty space around the breast between the compression plates). In the event only a single predefined tomosynthesis reconstruction algorithm is involved, the three-dimensional geometry of the imaged breast volume can be based upon the number of levels in that predefined tomosynthesis reconstruction algorithm. In the event multiple predefined tomosynthesis reconstruction algorithms are involved having different geometries, the three-dimensional geometry of the imaged breast volume can be based on one of them, with resampling being incorporated into the others to result in appropriate registration. Alternatively, the three-dimensional geometry of the imaged breast volume could be based on the tomosynthesis reconstruction algorithms that were, or will be, used to generate the "for presentation" tomosynthesis reconstructed images.

Navigation and Review of Displayed Tomosynthesis Image Set

Preferred embodiments of a tomosynthesis workstation employing an automated focus capability according to the presently disclosed inventions will now be described. It is to be appreciated by those skilled in the art that the particular components of the review workstation are described in a very basic (generic) fashion, and that the inventions disclosed herein may be practiced on any of a wide number, type and variety of computer (processor) controlled workstations including one or more processors and operatively associated or coupled user interface, display monitor, and memory components including computer executable instructions executable by the one or more processors, which are common place as of this time. As used herein, the terms "user" and "reviewer" are intended to be used interchangeably.

In particular, an exemplary system for navigating and reviewing a tomosynthesis image data set includes an image processor (e.g., a computer), an image display monitor operatively associated with the image processor; a memory operatively associated with or coupled to the image processor; and a user interface operatively coupled to the image processor and display monitor, wherein the user interface may in fact comprise in whole or part the display monitor (i.e., in a touch screen device such as a "tablet", "pod" or other "smart" device). The image processor is configured to display user-selected image slices from a tomosynthesis data set on the display monitor in response to one or more user commands received through the user interface. The image processor is further configured to detect through the user interface a user selection or indication of an object or region of interest in a then-displayed image from the data set (e.g., when the user positions a graphic arrow controlled by a "mouse device" over the respective object or region for a certain amount of time and/or affirmative actuates (e.g., by clicking) same while in that position.

Figure 3:
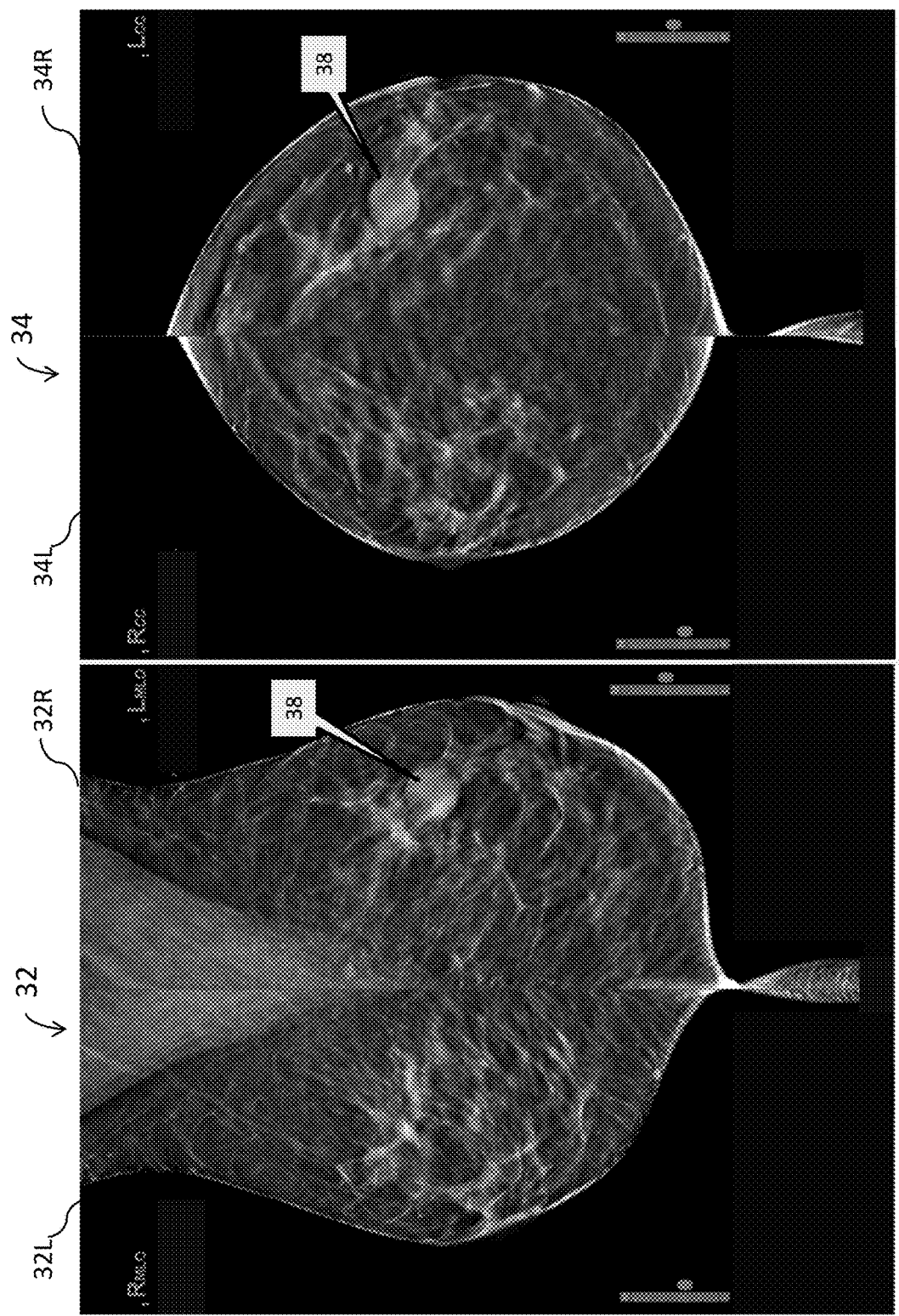
FIG. 3 depicts adjacent display monitors of an exemplary tomosynthesis image review workstation, including a left-hand monitor displaying respective $R_{MLO}$ and $L_{MLO}$ image slices; and a right-hand monitor displaying respective $R_{CC}$ and $L_{CC}$ image slices.

For purposes of more specific illustration, FIG. 3 depicts adjacent display monitors 32 and 34 of an exemplary tomosynthesis image review workstation 30, including a left-hand monitor 32 displaying respective right and left mediolateral oblique ("$R_{MLO}$" and "$L_{MLO}$") image slices 32L and 32R; and a right-hand monitor 34 displaying respective right and left craniocaudal ("$R_{CC}$" and "$L_{CC}$") image slices 34L and 34R. The $R_{MLO}$, $L_{MLO}$, $R_{CC}$, and $L_{CC}$ images are obtained from respective tomosynthesis image sets ("tomo stacks") containing right and left breast image data for each of the mediolateral oblique and craniocaudal orientations, for a total of four different tomo stacks. In particular, the displayed $R_{MLO}$ view is image 18 out of a 48 slice $R_{MLO}$ tomo stack; the displayed $L_{MLO}$ view is image 28 out of a 48 slice $L_{MLO}$ tomo stack; the displayed $R_{CC}$ view is image 18 out of a 48 slice $R_{CC}$ tomo stack; and the displayed $L_{CC}$ view is image 24 out of a 48 slice $L_{MLO}$ tomo stack. It will be appreciated by those skilled in the art that different tomo stacks may comprise differing numbers of image slices, and that the example tomo stacks having 48 image slices each are merely for example.

Notably, a round tissue mass 38 is visible in each of the $L_{MLO}$ and $L_{CC}$ image slices. It will be appreciated that the particular views of the tissue mass in the respective $L_{MLO}$ and $L_{CC}$ image slices differ in both clarity and orientation, since the image slices are taken along different (orthogonal) image planes, i.e., with the $L_{MLO}$ slice 28 comprising a cross-section taken along the z-axis of a "side view", and the $L_{CC}$ slice 24 comprising a cross-section taken along the z-axis of a top-down view that is orthogonal to the z-axis of the $L_{MLO}$ image set.

For purposes of simplifying the discussion, the remainder of the present specification refers just to the $L_{CC}$ (left breast craniocaudal) tomo stack, although the inventive concepts and features described apply equally to the navigation and review of any tomo image stack, as well as for other, non-breast, body tissue image volumes.

Figures 4, 4A:
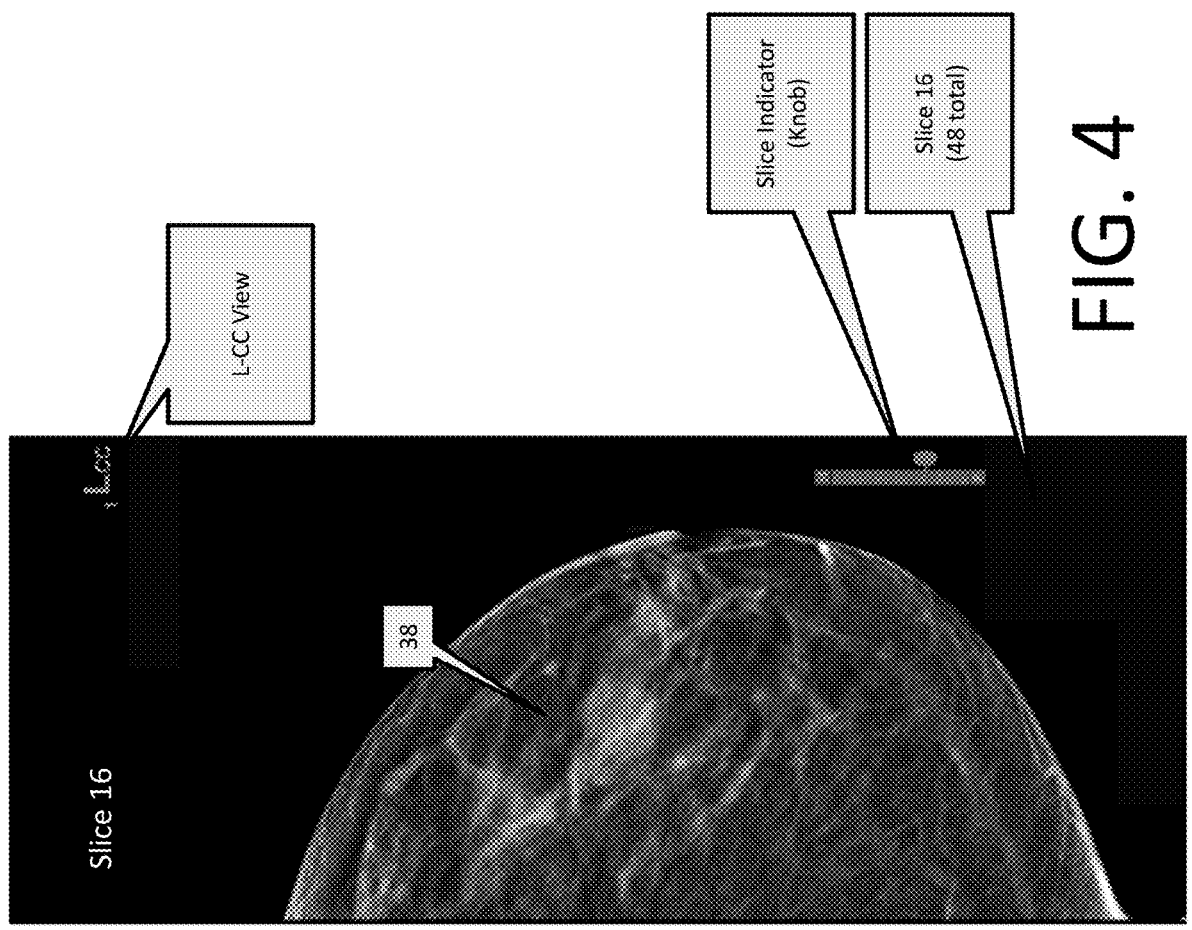
FIG. 4 depicts a single monitor displaying an $L_{CC}$ image slice from the same image set as the $L_{CC}$ image displayed in FIG. 3.
FIG. 4A is a close up view of a slice indicator that is displayed alongside the respective image slices that indicates the slice number of a presently-displayed image slice.

FIG. 4 depicts monitor 34L displaying $L_{CC}$ slice 16 of the same tomo stack as $L_{CC}$ slice 24 displayed in FIG. 3. The round mass 38 is visible in $L_{CC}$ slice 16, but is not as focused as in $L_{CC}$ slice 24 of FIG. 3, indicating that the actual location of the mass along the z-axis of the $L_{CC}$ tomo stack is closer to slice 24 than slice 16. As best seen in FIG. 4A, a slice indicator 40 including an animated "sliding knob" is provided at a lower right-hand corner of each display to provide the reviewer with the slice number (i.e., relative z-axis location) of a presently-displayed slice of a tomo stack. Thus, as the reviewer scrolls through the image slices of a tomo stack using a suitable user interface (i.e., computer mouse), the knob 42 on the slice indicator moves to reflect the currently displayed slice. An audible tone (e.g., a "clicking") may also be provided to indicate to the reviewer that the displayed slice has changes to a next one in the tomo stack.

Figure 5:
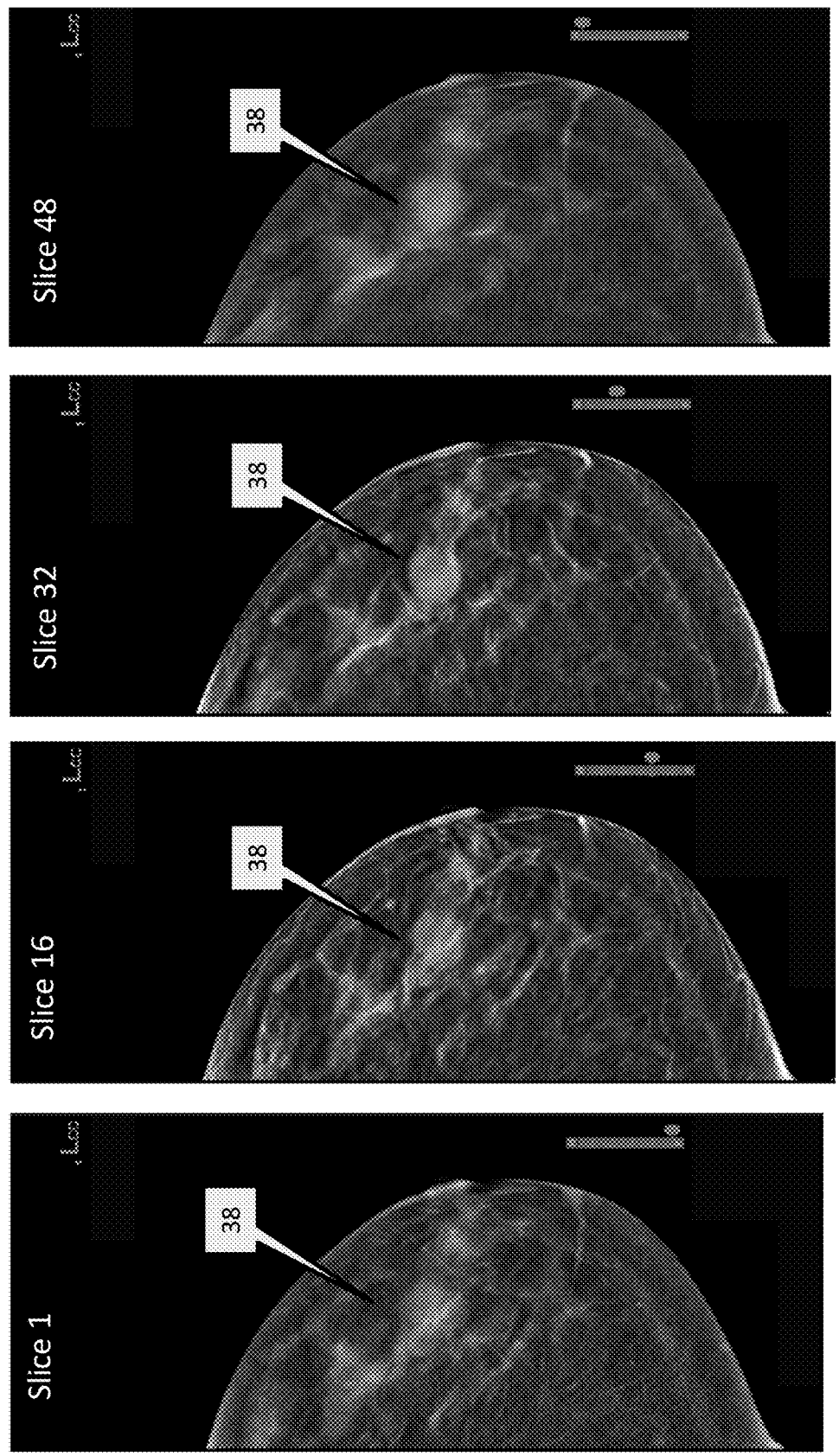
FIG. 5 depicts displayed $L_{CC}$ image slices obtained from the same tomosynthesis image set as the $L_{CC}$ images of FIGS. 3 and 4, illustrating a difference in visibility and clarity of a round tissue mass, depending on a relative z-axis location of the image slice.

In order to provide the perspective of the reviewer, FIG. 5 depicts the respective image slices 1, 16, 32 and 48 of the (same) $L_{CC}$ tomo stack as the images depicted in FIGS. 3 and 4, which clearly illustrate the differences in visibility and clarity of the round mass 38, depending on a relative z-axis location of the respective image slice. In particular, the mass is hard to make out in slice 1, but becomes more visible in slice 16, and is still more visible and clear (in terms of the edges, brightness, etc.) in slice 32, only to become blurred and difficult to make out in slice 48.

Figure 6:
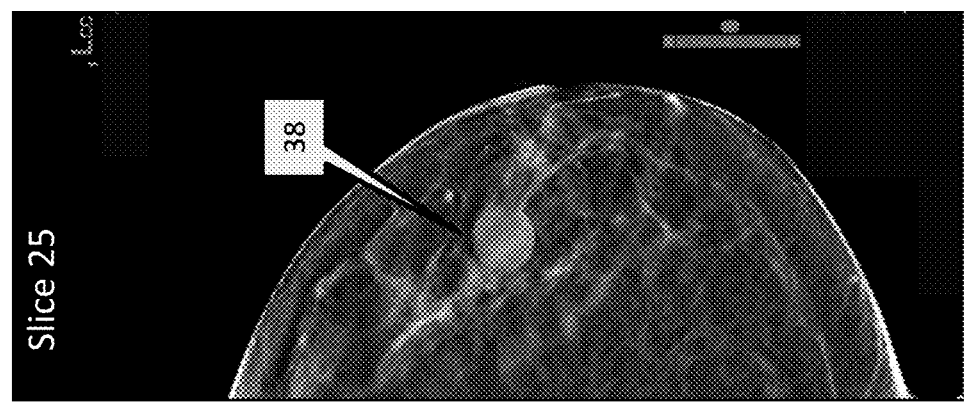
FIG. 6 depicts a displayed best focus $L_{CC}$ slice out of still the same tomosynthesis image set as FIGS. 3-5.

In one embodiment, the system detects through the user interface a user selection or indication of an object or region of interest in a then-displayed image from the tomo stack, and in response, displays an image from the data set having a best focus measure of the user selected or indicated object or region of interest. For example, FIG. 6 depicts a displayed "best focus" $L_{CC}$ image slice (slice 25) out of the (same) tomosynthesis image set with respect to the visibility and clarity of the round tissue mass 38. As explained in greater detail herein, the best focus slice 25 with respect to the tissue mass 38 was determined by the system processor based on a comparison of a computed focus measure of the tissue mass 38 for each image slice 1-48 of the $L_{CC}$ tomo stack. It is, of course, possible that the image slice displayed at the time the reviewer selects or otherwise indicates a particular object or region of interest make in fact turn out to be the image having the best focus of the user selected or indicated object or region of interest. In this case, the image processor may provide a visual or audible signal to the reviewer to indicate same (e.g., a beeping tone and/or highlighting of the object), since the image slice being displayed will not otherwise change.

Figure 7:
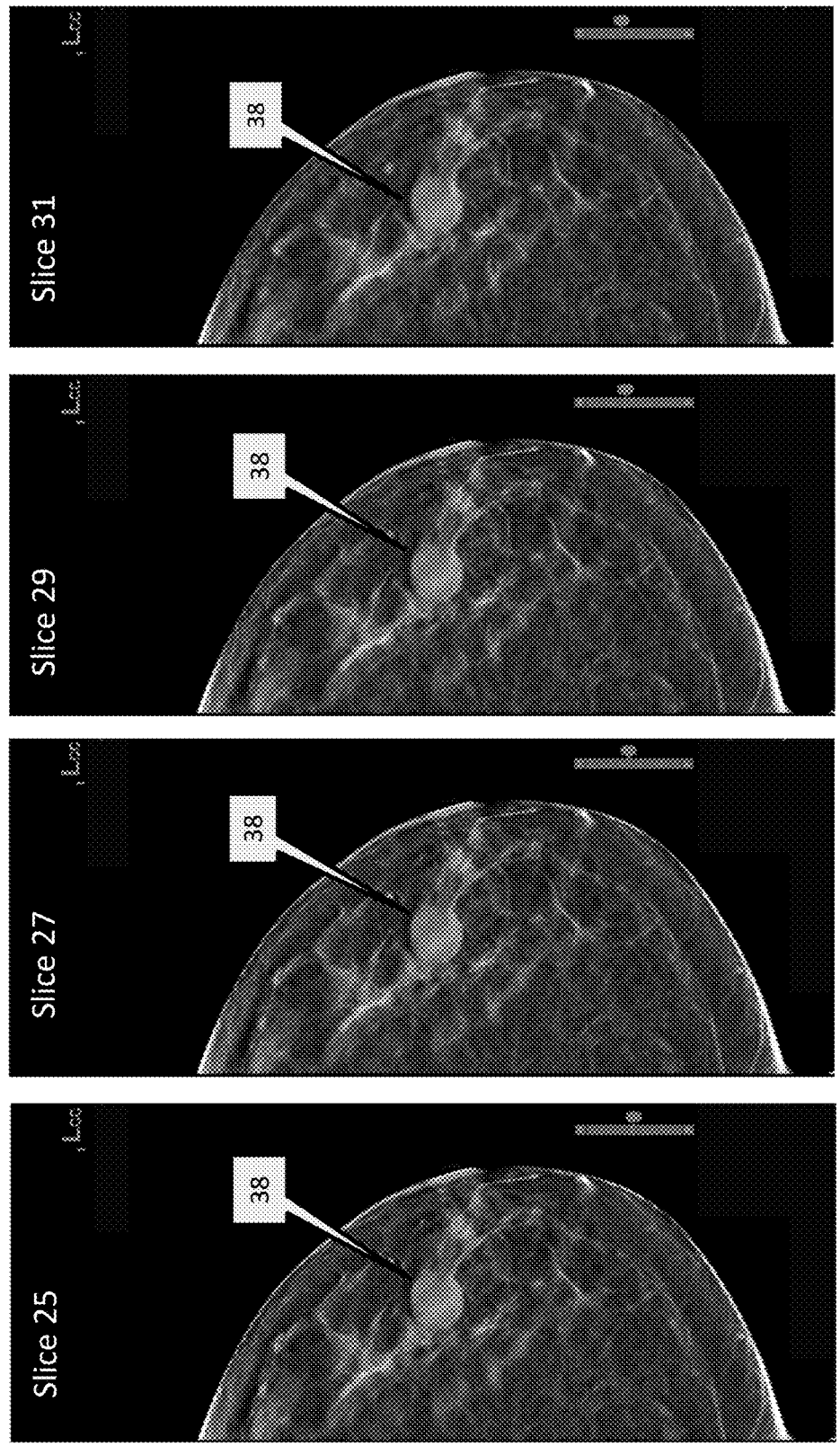
FIG. 7 depicts a series of displayed near-focus $L_{CC}$ slices from the (same) tomosynthesis image set, including the best focus image slice plus subsequent slices along the z-axis.

In another embodiment, the system detects through the user interface a user selection or indication of an object or region of interest in a then-displayed image from the tomo stack, and in response, displays a series of near-focus images from the data set on the display monitor, the series of near focus images comprising images of the data set having computed focus measure values within a predetermined range of, and including, a best focus measure value computed for any image of the data set depicting the user selected or indicated object or region of interest. For example, FIG. 7 depicts a series of displayed near-focus $L_{CC}$ image slices from the (same) tomosynthesis image set, including the best focus $L_{CC}$ slice 25, plus subsequent $L_{CC}$ slices 27, 29 and 31, demonstrating slight changes in visibility and clarity of the round tissue mass 38 as the respective image slices progress along the z-axis from the best-focused slice 25 (far left displayed image) to the relatively least-focused slice 31 (far right displayed image).

Figure 9:
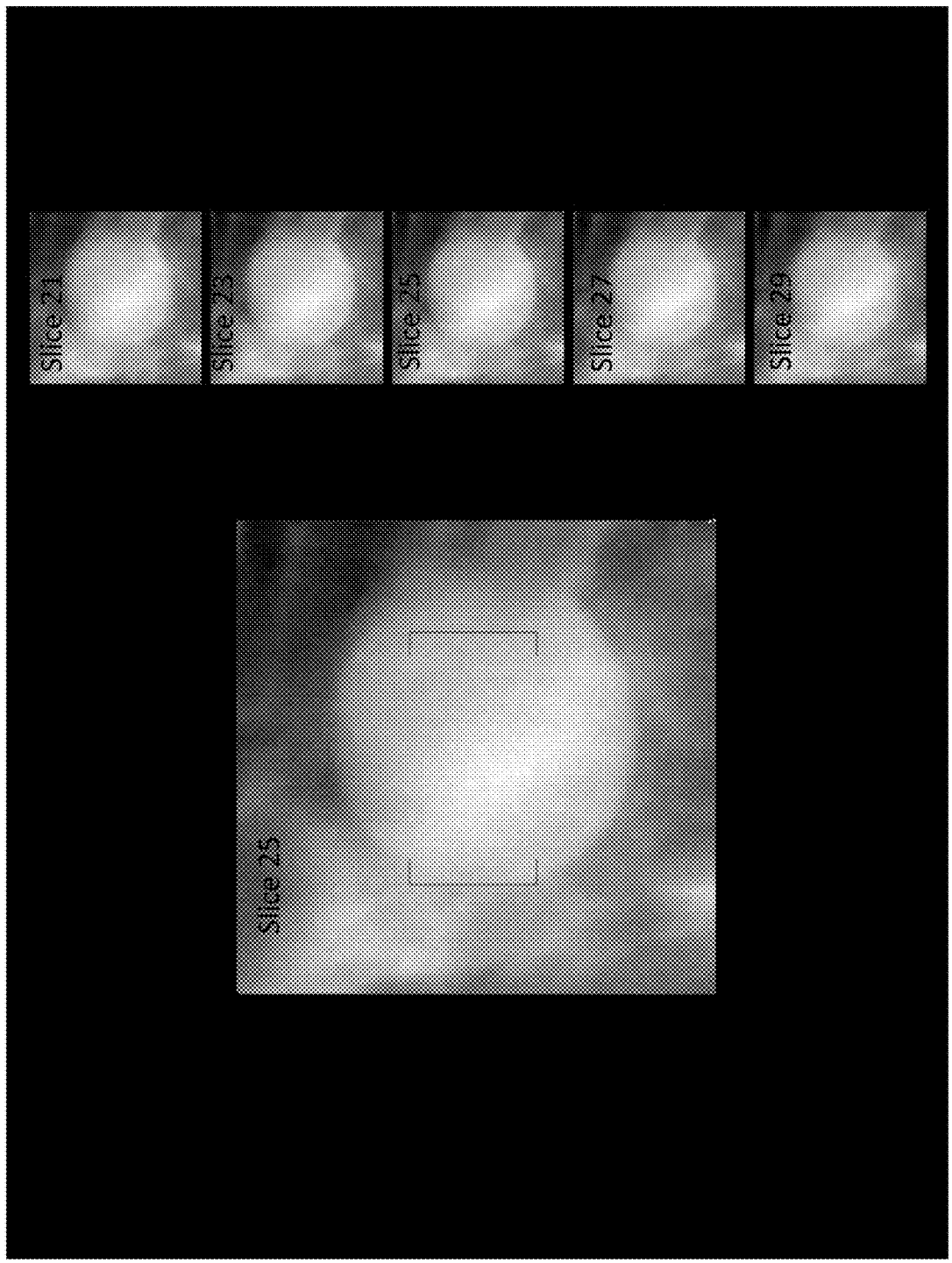
FIG. 9 depicts the displayed best focus $L_{CC}$ slice in a center area of the monitor, with the series of near-focus $L_{CC}$ slices displayed in a stacked formation alongside the best focus slice.

In one embodiment, such as depicted in FIG. 9, the series of near-focus images are displayed simultaneously, so as to allow for a static review and comparison of the user selected or indicated object or region of interest in each image of the near-focus series. In particular, FIG. 9 depicts the best focus $L_{CC}$ image slice 25 displayed in a center area of the monitor, with the subset near-focus $L_{CC}$ image slices 21, 23, 25, 27 and 29 displayed in a stacked formation alongside the best focus image slice 25 to allow the reviewer to see the changes in the tissue mass in each direction along the z-axis from slice 25.

In another embodiment, the series of near-focus of images are displayed in succession, so as to allow for a dynamic review and comparison of the user selected or indicated object or region of interest in each image of the near-focus series. For example, the images slices 25, 27, 29 and 31 of FIG. 7 may be automatically displayed in consecutive order, one at a time, and each for a predetermined amount of time (e.g., 1 second) in order to convey to the reviewer the changes in the object or region of interest along the z-axis of the tomo stack. This "video loop" functionality may be optionally configured to be repeated multiple times, and further optionally with the respective images slices displayed in a different order (e.g., lowest slice to highest, then reverse order) during different loop sequences. Preferably, specific parameters for displaying the images of a series of near-focus images is configurable through the user interface.

In some embodiments, in order to assist the reviewer, the system employs known image processing techniques to identify different breast tissue objects and structures in the various source images, and the reviewer may (optionally) cause the system to highlight such objects and structures in the respective best focus image and/or near-focus images, in particular, tissue structures comprising or related to abnormal objects, such as micro-calcification clusters, round-or-lobulated masses, spiculated masses, architectural distortions, etc.; as well as benign tissue structures comprising or related to normal breast tissues, such as linear tissues, cysts, lymph nodes, blood vessels, etc. For example, a user selected or indicated object or region of interest is highlighted by a contour line representing a boundary of the highlighted object or region. Furthermore, objects or regions of interest consisting of or including differing types of tissue structures may be highlighted in different manners when they are a respective subject of a focusing process.

Figure 8:
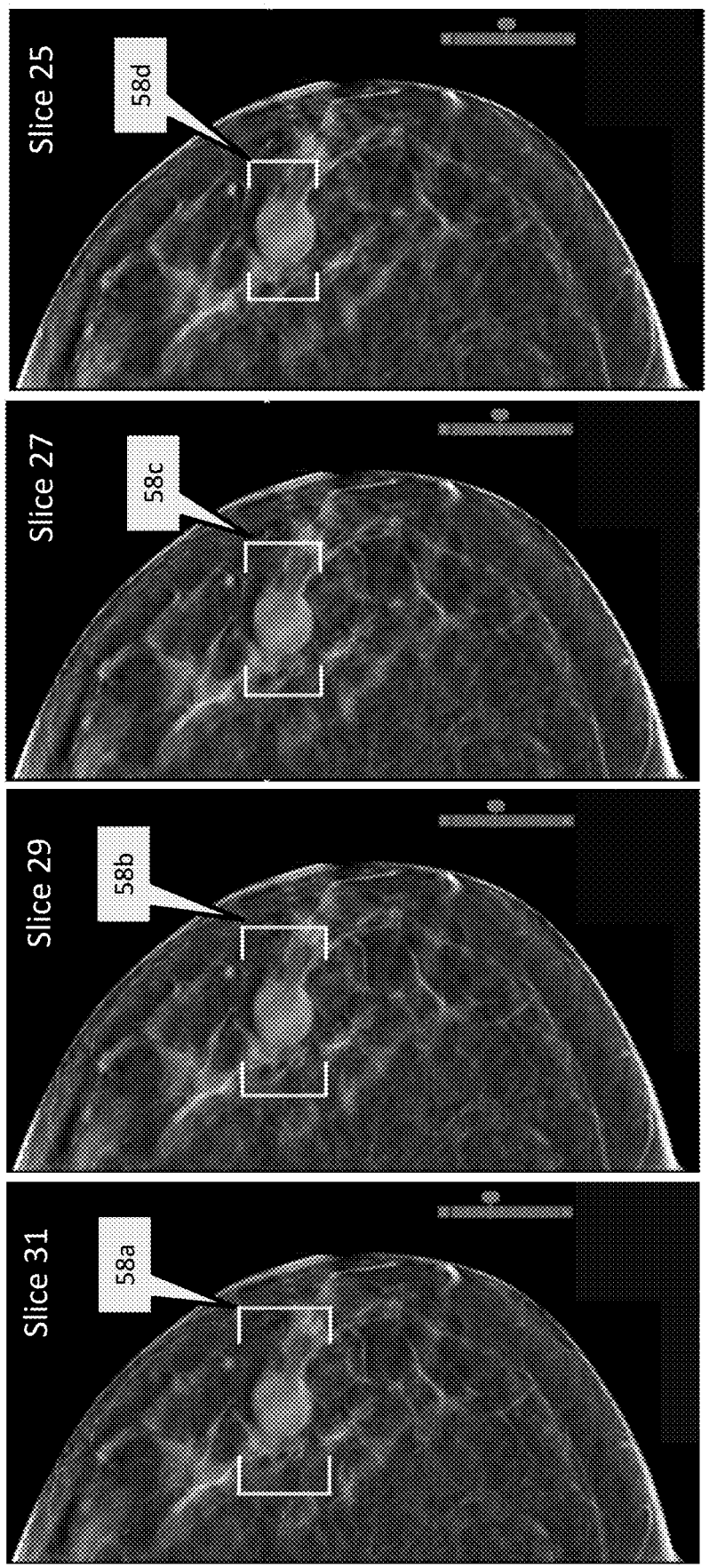
FIG. 8 depicts the series of displayed near-focus $L_{CC}$ image slices shown in FIG. 7, but in reverse order, wherein the round mass is highlighted with a visual indicia in the form of rectangular brackets.

By way of non-limiting illustration, FIG. 8 depicts the series of displayed near-focus $L_{CC}$ image slices shown in FIG. 7, but in reverse order, i.e., slices 31, 29, 27 and 25. wherein the round mass is highlighted with a visual indicia in the form of rectangular brackets 58a-d, which move progressively closer around the tissue mass 38, as the image slices progress along the z-axis from the relatively least-focused slice 31 (far left image) to best-focused slice 25 (far right image). Again, the presentation of the respective images slices of the series of near-focus images may be presented at the same time (for a static comparison), or in a video-loop style format, for a dynamic comparison.

Figure 10:
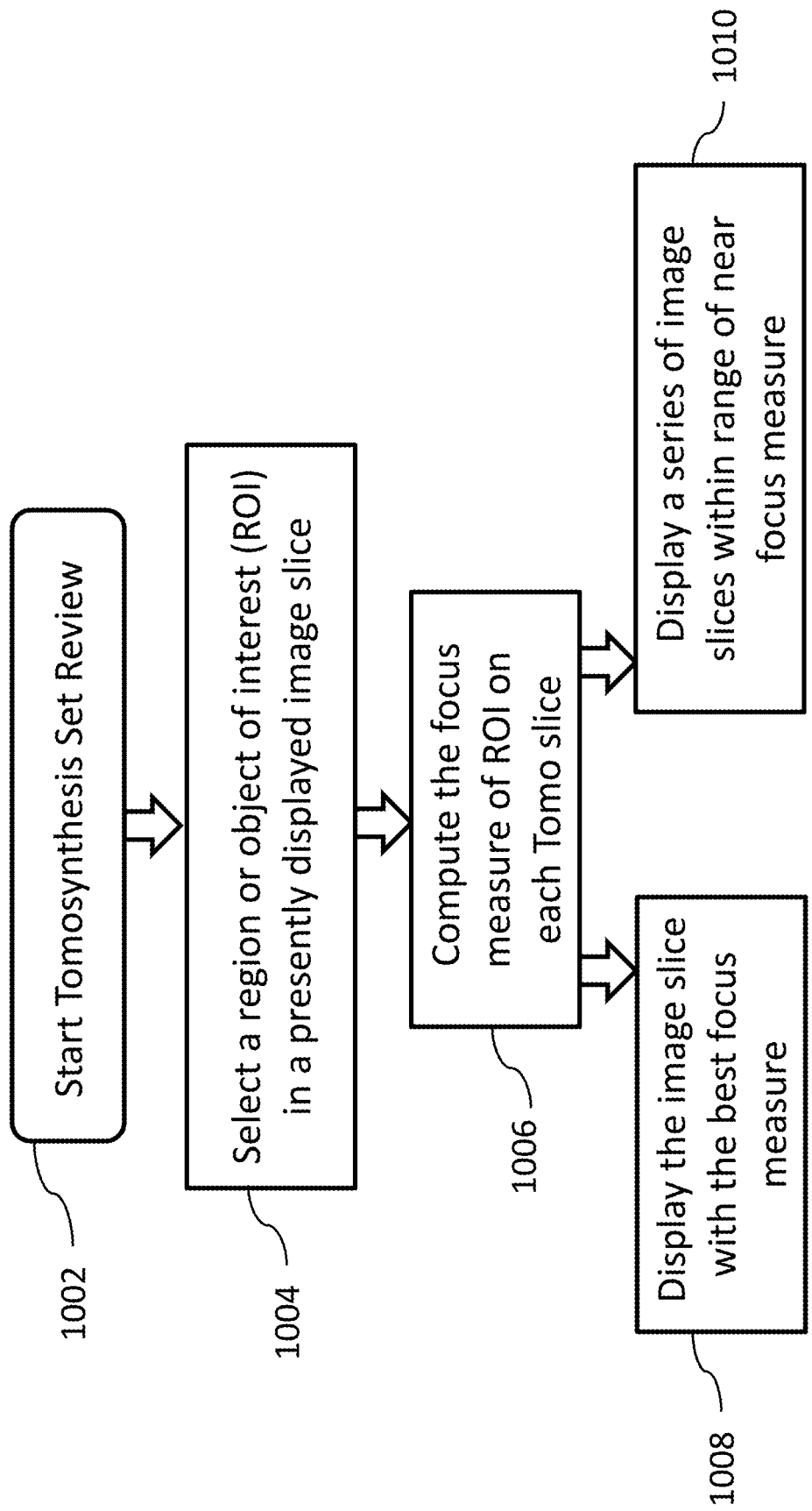
FIG. 10 is a flow diagram illustrating an exemplary process for displaying a best focus image slice or a series of near-focus slices of an object or region of interest in a tomosynthesis image set.

FIG. 10 is a flow diagram illustrating an exemplary process for displaying an image slice from a tomosynthesis data set having a best focus measure of a user selected or indicated object or region of interest in a previously displayed image slice from the set. Initially, at step 1002, the reviewer causes the system to initiate review of a tomosynthesis image set, e.g., of the prior illustrated and described $L_{CC}$ tomo stack having 48 slices. Thereafter, the reviewer scrolls through the image slices, typically but necessarily in an ascending order beginning at slice 1.

At step 1004, the reviewer selects or otherwise indicates an interest (i.e., for clinical evaluation) in an object or region of tissue in a then-displayed image slice of the tomo stack. Upon detecting the user selection or indication of an object or region of interest (hereinafter collectively referred to as "ROI" for purposes of describing the processes in FIGS. 10 and 11), at step 1006, the system thereafter computes a focus measure for the selected/indicated ROI in each image slice of the tomo stack.

As explained in greater detail below in conjunction with FIGS. 11 and 12, depending on the desired display protocol indicated by the reviewer, at step 1008, the system displays the image slice from the tomo stack having a best, (e.g., "highest" depending on the measuring protocol) focus measure out of all image slices of the tomo stack for the ROI. Alternatively or additionally, at step 1010, the system may display a series of near-focus image slices of the ROI, as described above. The range of slices that fall into a near-focus series may be pre-configured by the system, or user configurable. For example, a user may indicate through the user interface that the displayed series is include a selected number of images (e.g., five) out of the tomo stack having focus measures within a range of the five percent of one another and including the image having the best focus measure.

Figure 11:
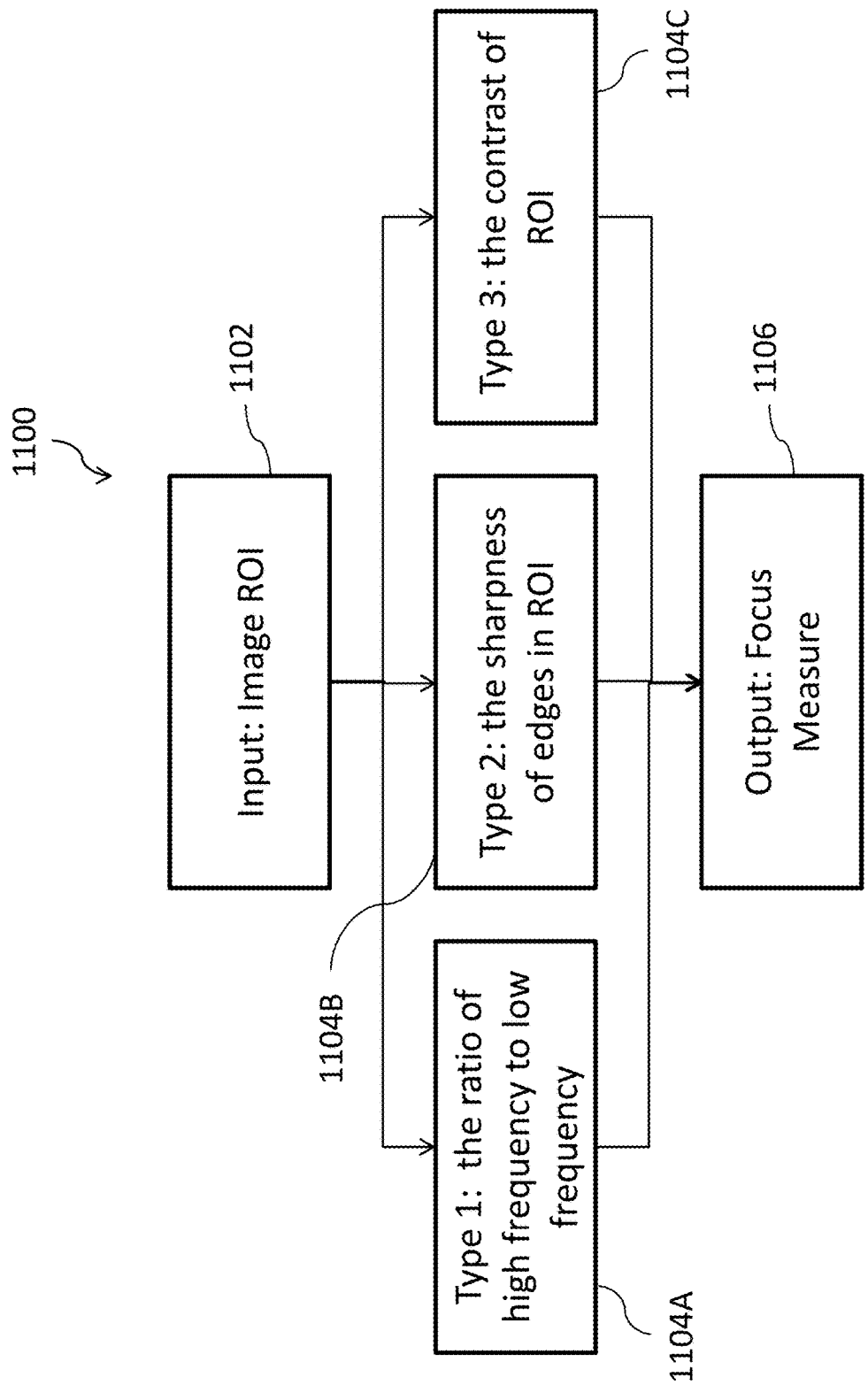
FIG. 11 is a flow diagram illustrating exemplary processes for computing a focus measure of an object or region of interest in a tomosynthesis image set.
Figure 12:
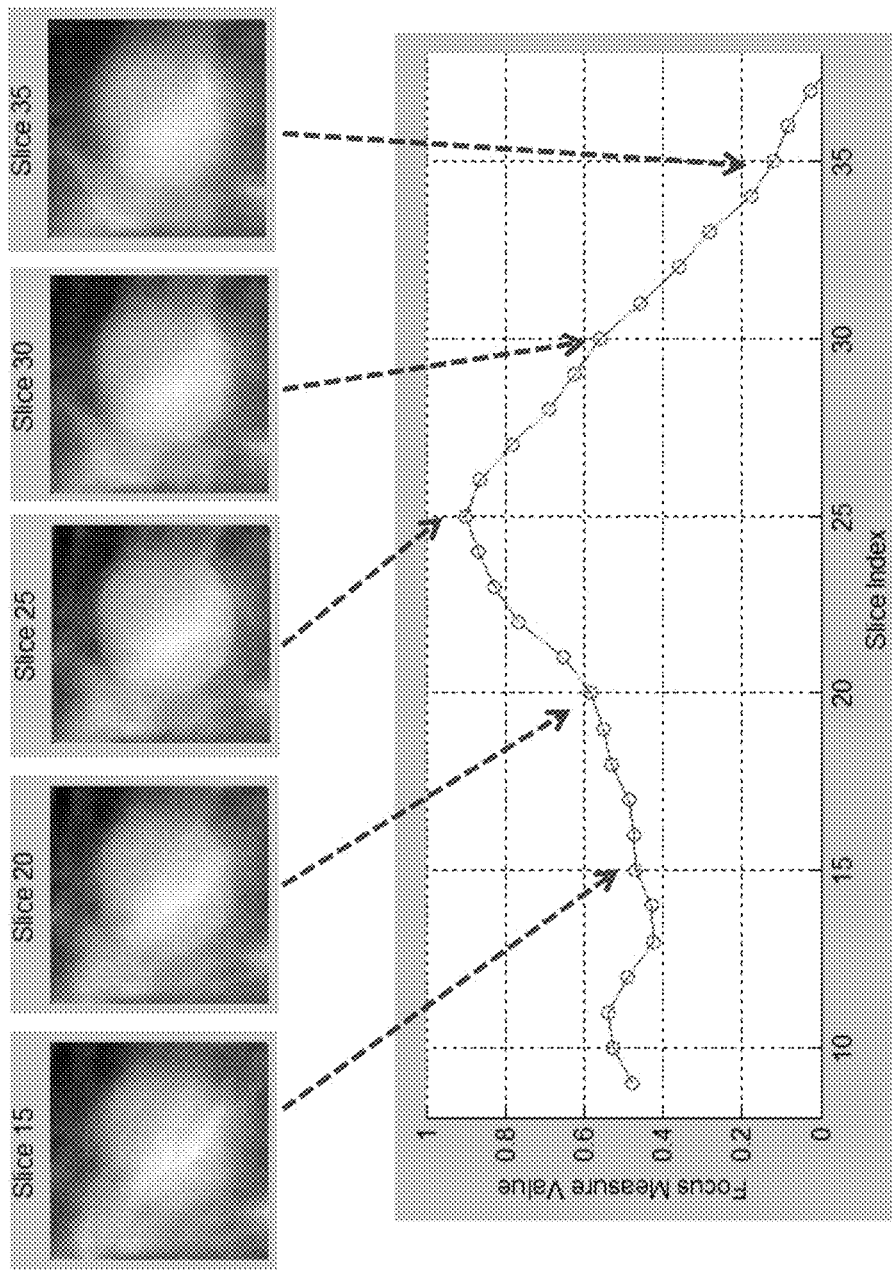
FIG. 12 illustrates a process for identifying an image having a highest relative focus measure of all images in a tomosynthesis image set with respective to a selected object or region of interest.

FIG. 11 is a flow diagram 1100 illustrating exemplary processes for computing a focus measure of a user selected or indicated object or region of interest in a displayed image slice of a tomosynthesis image set. As discussed above, the process begins, at step 1102, upon the reviewer selecting or otherwise indicating an ROI in a presently displayed (or "then-displayed") image slice. The image slice having a best focus measure of the ROI out of the entire tomo stack is then determined by the system based on a comparison of a focus measure of the ROI for each image slice of the tomo stack.

In accordance with the presently disclosed inventions, a determination of focus score and, thus, a best focus score, may be accomplished in a number of ways including, at step 1104A, wherein the focus measure is computed according to known image processing techniques based on a sharpness of detected edges of the object or region of interest. For example, the total gradient magnitude of detected edges inside region of interest is a known measure for sharpness of detected edges. Alternatively and/or additionally, at step 1104B, the focus measure may be computed according to known image processing techniques based on a computed contrast of the object or region of interest, wherein the contrast can be defined as the absolute difference of a pixel with its eight neighbors, summed over all the pixels in region of interest. Alternatively and/or additionally, at step 1104C, the focus measure may be computed according to known image processing techniques based on a ratio between a measured magnitude of one or more high frequency components and a measured magnitude of one or more low frequency components, wherein high frequency components correspond to sharp edges of the object in the foreground, while low frequency components correspond to a blur area in the background. A high value of the ratio between a measured magnitude of high frequency components and a measured magnitude of low frequency components indicates that the object or region of interest is in focus.

Once the focus measure for each slice has been determined, at step 1106, the system may cause to be displayed the image slice having the best focus measure score and/or a series of images having focus measures within a predetermined range, e.g., within 5% of the best focus measure. This process is illustrated for the above-described and illustrated $L_{CC}$ tomo stack in FIG. 12, which depicts for purposes of illustration respective computed focus measure values of the round tissue mass 38 for images slices 15, 20, 25, 30 and 35, progressing along the z-axis of the $L_{CC}$ tomo image stack. In particular, the focus measure scores plotted in the graph of FIG. 12 were computed using a ratio between the measured magnitude of high frequency components and the measured magnitude of low frequency components within the selected image ROI. As can be seen, image slice 25 has the highest focus measure value, which in this case also means the "best" focus measure.

Having described exemplary embodiments, it can be appreciated that the examples described above and depicted in the accompanying figures are only illustrative, and that other embodiments and examples also are encompassed within the scope of the appended claims. For example, while the flow diagrams provided in the accompanying figures are illustrative of exemplary steps; the overall image merge process may be achieved in a variety of manners using other data merge methods known in the art. The system block diagrams are similarly representative only, illustrating functional delineations that are not to be viewed as limiting requirements of the disclosed inventions. Thus the above specific embodiments are illustrative, and many variations can be introduced on these embodiments without departing from the scope of the appended claims.

The invention claimed is:

1. An automated method employing a computer-controlled workstation for navigating and displaying breast tissue images, the workstation comprising an operatively associated user interface and display monitor, the method comprising:
    obtaining a tomosynthesis image data set, the data set comprising volumetric image data of a breast;
    displaying a series of images from the data set on the display monitor in response to one or more user commands received through the user interface;
    detecting, through the user interface, input by a user of the workstation selecting or indicating a region of interest in a currently displayed image;
    highlighting the region of interest with a visual indicia comprising a geometric shape in at least one image of the series of images; and
    in response to the user input, continuing to highlight the region of interest in respective other images of the series as the respective other images are displayed;
    computing respective focus measures of an object in the region of interest in the series of images;
    comparing the determined focus measures of the object in the region of interest for the series of images to one other;
    based on the comparison, determining a desired focus measure for an image of the series of images; and
    displaying the image having the desired focus measure and a plurality of other images of the series of images, the other images having focus measures that are within a predetermined range of the desired focus measure.

2. The method of claim 1, wherein the respective focus measures are computed based upon one or more of:
    a sharpness of detected edges of the region of interest,
    a contrast of the region of interest, and
    a ratio between a measured magnitude of one or more high frequency components and a measured magnitude of one or more low frequency components.

3. The method of claim 1, wherein each image of the image data set is a tomosynthesis reconstructed image, detecting user input comprises detecting user input selecting or indicating the region of interest in a currently displayed tomosynthesis reconstructed image, and each additional image that is displayed while continuing to highlight the region of interest in respective images is a tomosynthesis reconstructed image of the image data set.

4. The method of claim 1, wherein the user selected or indicated region of interest is highlighted in a manner indicating that the region includes a specified type of tissue structure.

5. The method of claim 1, wherein the images of the series of images are displayed in succession.

6. The method of claim 1, wherein the desired focus measure is a best focus measure.

7. A system for navigating and displaying breast tissue images, the workstation comprising:
    an operatively associated user interface;
    a display;
    at least one processor; and
    a memory coupled to the at least one processor, the memory comprising computer executable instructions that, when executed by the at least one processor, perform a method comprising:
        obtaining a tomosynthesis image data set, the data set comprising volumetric image data of at least a portion of a breast;
        displaying a series of images from the data set on the display;
        detecting, through the user interface, an input by a user selecting or indicating a region of interest in an image that is one of the series of images and currently displayed on the display;
        highlighting on the display, in response to the input by the user, the region of interest with a visual indicia comprising a geometric shape; and
        displaying on the display other images of the series while continuing to highlight the region of interest with the visual indicia in each of other images of the series as the each of the images is displayed;
    computing respective focus measures of an object in the region of interest in the series of images;
    comparing the determined focus measures of the object in the region of interest for the series of images to one other;

based on the comparison, determining a desired focus measure for an image of the series of images; and displaying the image having the desired focus measure and a plurality of other images of the series of images, the other images having focus measures that are within a predetermined range of the desired focus measure.

8. The system of claim 7, wherein the respective focus measures comprising respective single focus measure values calculated for the region of interest in the respective images.

9. The system of claim 8, wherein each of the focus measures are computed based upon one or more of:
   a sharpness of detected edges of the region of interest,
   a contrast of the region of interest, and
   a ratio between a measured magnitude of one or more high frequency components and a measured magnitude of one or more low frequency components.

10. The system of claim 9, wherein the user selected region of interest is highlighted in a manner indicating that the region includes a specified type of tissue structure.

11. The system of claim 9, wherein the images of the series of images are displayed in succession.

12. The system of claim 7, wherein geometric shape comprises a rectangular shape.

13. The system of claim 7, wherein the desired focus measure is a best focus measure.

14. A method for navigating and displaying breast tissue images, the method comprising:
   obtaining a tomosynthesis image data set, the data set comprising volumetric image data of at least a portion of a breast;
   displaying a series of images from the data set on a display of a computer-controlled workstation;
   detecting, through a user interface associated with the computer-controlled workstation, an input by a user selecting or indicating a region of interest in an image that is one of the series of images and currently displayed on the display;
   highlighting on the display, in response to the input by the user, the region of interest with a visual indicia comprising a geometric shape; and
   displaying on the display other images of the series while continuing to highlight the region of interest with the visual indicia in each of other images of the series as the each of the images is displayed;
   computing respective focus measures of an object in the region of interest in the series of images;
   comparing the determined focus measures of the object in the region of interest for the series of images to one other;
   based on the comparison, determining a desired focus measure for an image of the series of images; and
   displaying the image having the desired focus measure and a plurality of other images of the series of images, the other images having focus measures that are within a predetermined range of the desired focus measure.

15. The method of claim 14, wherein the respective focus measures comprising respective single focus measure values calculated for the region of interest in the respective images.

16. The method of claim 15, wherein each of the respective focus measures is computed based upon one or more of:
   a sharpness of detected edges of the region of interest,
   a contrast of the region of interest, and
   a ratio between a measured magnitude of one or more high frequency components and a measured magnitude of one or more low frequency components.

17. The method of claim 14, wherein each of the displayed images of the image data set is a tomosynthesis reconstructed image, detecting user input comprises detecting user input selecting or indicating the region of interest in a currently displayed tomosynthesis reconstructed image, and each additional image that is displayed while continuing to highlight the region of interest in respective images is a tomosynthesis reconstructed image of the image data set.

18. The method of claim 14, wherein the geometric shape comprises a rectangular shape.

19. The method of claim 14, wherein the user selected or indicated region of interest is highlighted in a manner indicating that the region includes a specified type of tissue structure.

20. The method of claim 14, wherein the display the images of the series of images comprises displaying the images in succession.

21. The method of claim 14, wherein the desired focus measure is a best focus measure.

* * * * *